US008372616B2

(12) United States Patent
Sando et al.

(10) Patent No.: US 8,372,616 B2
(45) Date of Patent: Feb. 12, 2013

(54) HOMOGENTISIC ACID GERANYLGERANYL TRANSERASE POLYPEPTIDE

(75) Inventors: Tomoki Sando, Tokyo (JP); Norie Watanabe, Tokyo (JP); Koichiro Gyokusen, Fukuoka (JP); Eiichiro Fukuzaki, Osaka (JP); Akio Kobayashi, Osaka (JP); Haska Nadirman, Jakarta (JP); Purbowasito Wahyu, Jakarta (JP)

(73) Assignees: Bridgestone Corporation, Tokyo (JP); Badan Pengkajian Dan Penerapan Teknologi, Jakarta (IN)

( * ) Notice: Subject to any disclaimer, the term of this patent is extended or adjusted under 35 U.S.C. 154(b) by 314 days.

(21) Appl. No.: 12/593,184

(22) PCT Filed: Mar. 19, 2008

(86) PCT No.: PCT/JP2008/055148
§ 371 (c)(1),
(2), (4) Date: Dec. 10, 2009

(87) PCT Pub. No.: WO2008/117731
PCT Pub. Date: Oct. 2, 2008

(65) Prior Publication Data

US 2010/0186109 A1 Jul. 22, 2010

(30) Foreign Application Priority Data

Mar. 27, 2007 (JP) ................................ 2007-082184

(51) Int. Cl.
*C12N 9/10* (2006.01)
(52) U.S. Cl. ...................................................... 435/193
(58) Field of Classification Search ........................ None
See application file for complete search history.

(56) References Cited

FOREIGN PATENT DOCUMENTS

| | | | |
|---|---|---|---|
| JP | 61210030 | A | 9/1986 |
| JP | 2005-130815 | A | 5/2005 |
| JP | 2006-75106 | A | 3/2006 |
| WO | 00/32757 | A2 | 6/2000 |
| WO | 01/79472 | A2 | 10/2001 |
| WO | 03082899 | A2 | 10/2003 |

OTHER PUBLICATIONS

Sasaki et al; (GenBank Sequence Accession No. Q6Z3Y3; IDS; Published Oct. 31, 2006).*
Shaull et al. (GenBank Sequence Accession No. Q1SRL6; Published Oct. 31, 2006).*
Cahoon et al. (Nature Biotechnology, 21(9):1082-1097, 2003).*
Dictionary definition of "represent", obtained from education.yahoo.com/reference/dictionary/entry/represent, last viewed on Jan. 31, 2012, 1 page.*
Sigma Catalog, 1997, p. 1089.*
International Search Report dated Apr. 22, 2008 in corresponding International Application No. PCT/JP2008/055148.
"Acesion: Q6Z3Y3 [GI:752537], Definition: Putative prephenate dehydratase (0s07g069460 protein)." NCBI Sequence Revision History [online]; Oct. 31, 2006 uploaded, NCBI, <URL:http://www.ncbi.nlm.nih.gov/entrez/viewer.fcgi?db=protein&id=75225337> [retrieved on Apr. 9, 2008] Retrieved from the Internet: <URL:http://www.ncbi.nlm.nih.gov/entrez/sutils/girevhist.cgi?val=Q6Z3Y3>.
"Acesion: Q8LFI1 [Gi:75246068], Definition: Putative P-protein: chorismate mutase, prephenate dehydratase." NCBI Sequence Revision History [online]; Oct. 31, 2006 uploaded, NCBI, <URL:http://www.ncbi.nlm.nih.gov/entrez/viewer.fcgi?75246068:CAGE_DDBJ:12622834> [retrieved on Apr. 9, 2008] Retrieved from the Internet<URL: http://www.ncbi.nlm.nih.gov/entrez/sutils/girevhist.cgi?val=Q8LFI1>.
"Acesion: Q1SRL6 [GI:121904], Definition: Prephenate dehydratase with ACT region." NCBI Sequence Revision History [online]; Oct. 31, 2006 uploaded, NCBI, <URL:http://www.ncbi.nlm.nlh.gov/entrez/viewer.fcqi?122190444:CAGE_DDBJ:12509326> [retrieved on Apr. 9, 2008] Retrieved from the Internet: <URL:http://www.ncbi.nlm.nih.gov/entrez/sutils/girevhist.cgi?val=Q1SRL6>.
"Acesion: Q650V6 [GI:7514204], Definition: Putative prephenate dehydratase. "NCBI Sequence Revision History [online]; Oct. 31, 2006 uploaded, NCBI, <URL:http://www.ncbi.nlm.nih.gov/entrez/viewer.fcqi?75114204:CAGE_DDBJ:12565455> [retrieved on Apr. 9, 2008] Retrieved from the Internet: <URL:http://www.ncbi.nlm.nih.gov/entrez/sutils/girevhist.cgi?val=Q650V6>.
"Acesion: Q8LAP1 [GI:75154824], Definition: Putative chorismate mutase/prephenate dehydratase." NCBI Sequence Revision History [online]; Oct. 31, 2006 uploaded, NCBI, <URL:http://www.ncbi.nlm.nih.gov/entrez/viewer._fcqi?75154824:CAGE_DDBJ:12621626> [retrieved on Apr. 9, 2008] Retrieved from the Internet: <URL:http://www.ncbi.nlm.nih.gov/entrez/sutils/girevhist.cgi?val=Q8LAP1>.
"Acesion: Q6JJ29 [Gi:75124194], Definition: Prephenate dehydratase." NCBI Sequence Revision History [online]; Oct. 31, 2006 uploaded, NCBI. <URL:http://www.ncbi.nlm.nih.gov/entrez/viewer.fcqi?75124194:CAGE_DDBJ:12578702> [retrieved on Apr. 9, 2008] Retrieved from the Internet: <http://www.ncbi.nlm.nih.gov/entrez/sutils/girevhist.cgi?val=Q6jj29>.
I. Garcia, et al., "Characterization and Subcellular Compartmentation of Recombinant 4-Hydroxyphenylpyruvate Dioxygenase from *Arabidopsis* in Transgenic Tobacco," Plant Physiology, Apr. 1999, pp. 1507-1516, vol. 119, No. 4.
J. Imsande, et al., "A Soybean Plastid-Targeted NADH-Malate Dehydrogenase: Cloning and Expression Analyses," American Journal of Botany, 2001, pp. 2136-2142, vol. 88, No. 12.

(Continued)

*Primary Examiner* — David J Steadman
(74) *Attorney, Agent, or Firm* — Sughrue Mion, PLLC

(57) ABSTRACT

It is a subject of this invention to isolate a gene group of enzymes involved in the biosynthesis of vitamin E of Para rubber tree, and to determine the base sequence of each gene. According to this invention, genes encoding enzymes involved in the vitamin E biosynthesis were isolated from Para rubber tree and the base sequences of these genes were determined. Since vitamin E is an antioxidant existing in nature, it is expected that transformation of a plant by using the genes obtained in the invention would result in an increase in the vitamin E content of the plant and, in its turn, contribute to the prevention of rubber from aging.

1 Claim, 25 Drawing Sheets

OTHER PUBLICATIONS

T.V. Venkatesh, et al., "Identification and characterization of an *Arabidopsis* homogentisate phytyltransferase paralog," Planta, 2006, pp. 1134-1144, vol. 223.

S. Tang, et al., "*Ty3lgypsy*-like retrotransposon knockout of a 2-methyl-6-phytyl-1, 4-benzoquinone methyltransferase is non-lethal, uncovers a cryptic paralogous mutation, and produces novel tocopherol (vitamin E) profiles in sunflower," Theor. Appl. Genet., 2006, pp. 783-799, vol. 113.

E.B. Cahoon, et al., "Metabolic redesign of vitamin E biosynthesis in plants for tocotrienol production and increased antioxidant content," Nature Biotechnology, Sep. 2003, pp. 1082-1087, vol. 21, No. 9.

Z. Cheng, et al., "Highly Divergent Methyltransferases Catalyze a Conserved Reaction in Tocopherol and Plastoquinone Synthesis in Cyanobacteria and Photosynthetic Eukaryotes," The Plant Cell, Oct. 2003, pp. 2343-2356, vol. 15.

D. Hofius, et al., "RNAi-Mediated Tocopherol Deficiency Impairs Photoassimilate Export in Transgenic Potato Plants," Plant Physiology, Jul. 2004, pp. 1256-1268, vol. 135, No. 3.

"Acesion: Q2XV81 [GI:122211059], Definition: Tocopherol cyclase." NCBI Sequence Revision History [online]; Oct. 31, 2006 uploaded, NCBI, <URL:http://www.ncbi.nlm.nih.gov/entrez/viewerfcgi?122211059:CAGE_DDBJ:12529946> [retrieved on Apr. 9, 2008] Retrieved from the Internet: <http://www.ncbi.nlm.nih.gov/entrez/sutils/girevhist.cgi?val=Q2XV81>.

F. Bouvier, et al., "Biogenesis, molecular regulation and function of plant isoprenoids," Progress in Lipid Research, 2005, pp. 357-429, vol. 44, No. 6.

E. Collakova, et al., "The Role of Homogentisate Phytyltransferase and Other Tocopherol Pathway Enzymes in the Regulation of Tocopherol Synthesis during Abiotic Stress," Plant Physiology, Oct. 2003, pp. 930-940, vol. 133.

K. J. Whittle, et al., "The Isolation and Properties of δ-Tocotrienol from *Hevea* Latex," Biochem. J., 1966, pp. 138-145, vol. 100.

Dunphy, et al., "Identification and Estimation of Tocotrienols in *Hevea* Latex," Nature, Jul. 31, 1965, pp. 521-522, vol. 207.

Y. Keller, et al., "Metabolic Compartmentation of Plastid Prenyllipod Biosynthesis—Evidence for the involvement of a multifunctional geranylgeranyl reductase," Eur. J. Biochem., 1998, pp. 413-417, vol. 251.

S. E. Sattler, "Characterization of Tocopherol Cyclases from Higher Plants and Cyanobacteria. Evolutionary Implications for Tocopherol Synthesis and Function," Plant Physiology, Aug. 2003, pp. 2184-2195, vol. 132.

M. Schledz, et al., "A Novel phytyltransferase from *Synechocystis* sp. PCC 6803 involved in tocopherol biosynthesis," Federation of European Biochemical Societies Letter 499, 2001, pp. 15-20.

D. Shintani, et al., "Elevating the Vitamin E Content of Plants Through Metabolic Engineering," Science, Dec. 11, 1998, pp. 2098-2100, vol. 282.

A. L. Van Eenennaam, et al., "Engineering Vitamin E Content: from *Arabidopsis* Mutant to Soy Oil," The Plant Cell, Dec. 2003, pp. 3007-3019, vol. 15.

European Patent Office, "Supplementary European Search Report," issued in connection with European Patent Application No. 08722522.3, dated Jun. 1, 2010.

Horvath et al., "Differential Distribution of Tocopherols and Tocotrienols in Photosynthetic and Non-Photosynthetic Tissues," Phytochemistry, Pergamon Press, GB Lnkd, vol. 67, No. 12, pp. 1185-1195, Jun. 1, 2006.

European Communication dated May 5, 2012, for European Application No. 08 722 522.3.

* cited by examiner

FIG. 2

PD 02730 prephenate dehydratase 1-1677bp ORF: 160-1329bp

GACGGCACAAAGCCAACCCACCTTCTGTAAAACTATACTTCCGTACTTCGGACGTC
TAGCCTTTTTCTCCTTTTCTCACCGCCTCCACTTTCCTCAGACTTTACAAATATCCC
TCTCTCTCTCTCTCTCTCTCTCTCATGCACCTTGCCTAACTCATCAATGGCGCCTTT
TGTTATACGGTCTCTTGTTAACCTTCCGGGCCAAATCGCCGTTAAACACTTGCCAAC
TGATCAATTTCCCAGAATTGAAATCAAATTGCCGCTGATTTTGGTTAAACCGCGACA
TAATACGATTGTTTTGGCCTCTCTTCATGGAGAAAACGAGAGAGCAATCGAGGCTG
ACGGGAAGAACACTCAGACTGCTCTTCAATTGCAGGATTCTCCTTACGACGTCGTT
TCCAGAGATGCGCTCCCGAGGCCGTTATCTTCTTCTCAATCCTCCAGTTCGGTCTC
TGATGGGTCACGTCTTCGCGTTGCTTACCAGGGAGTTCGTGGCGCGTACAGCGAAT
CAGCGGCCGAGAAAGCCTATCCGAATTGCGAAGCAGTACCGTGTGAGCAATTTGA
CGCGGCTTTTGAGGCTGTTGAACGATGGCTTGTGGACAGAGCAGTTTTGCCCATTG
AGAATTCCTTAGGTGGGAGCATCCACAGAAATTATGACCTTTTGCTCCGTCATAGA
CTGCATATAGTAGGGGAAGTGAAATATGCTGTTCGCCATTGCTTACTAGCCAATCAT
GGTGTTAAAGTTGAAGACTTGAAGAGGGTCCTAAGTCATCCGCAGGCCCTTGCTCA
ATGTGAGCATACATTAACAAGTTTGGGATTGGTTAGAGAAGCAGTGGATGATACTG
CTGGTGCAGCAAAGCATGTTGCACTTCACAAACTGAAAGACACAGGAGCTGTTGCT
AGTTCTGTGGCTGCAAAGATTTATGGGTTGAATATATTAGCTGAAGATATTCAGGAT
GATTGTGATAATGTTACTCGGTTTCTGATGCTAGCCAGGGAGCCAATAATCCCAGG
AACGGACAGGCCATTCAAGACGAGCATTGTTTTTTCACTTGAGGAGGGTCCTGGA
GTGCTTTTCAAAGCACTTGCTGTTTTTGCTTTGCGGCAAATCAACCTTACTAAGATT
GAGAGTCGTCCATTGCGGAACCAGCCCTTGAGAGCATCTGATGATAGCGACAATGG
GTTTCCAAAATACTTTGACTATCTTTTCTATGTGGATTTTGAGGCATCAATGGCCGA
CCAGAATGCACAGAATGCCCTCAAGCACCTGAAGGAGTTTGCGACTTTCTTACGAG
TTTTGGGGAGTTATCCAGTGGATACTAGCATGATATAAATGATCCTCTAACACGGGG
CCTGGAGGAAAAAAATTACCCTGATAAGAACGGAAGCACTGATGATATTCCTTTTT
CAAATTTATCACTAAATGGATGCAGCAAAACTTGATCTATCGCCATTTCATCCAATT
TTGTAGTGTCTTCTCAATACTGCACATGTAATTAAGAGTTAATCGGGTATTTTTATAG
AGGTTGTTATTTCTTTCGTGCTTGGCAATTTTTTCTGTGGGTTCACTTACGTGTCAC
CAATGTTGGGCATGACATACCAAAATGCTGTACAAGAGAAGTTACAAATTCAAATTC
TTTCTTTCCTTTTTAGTGTTTGATTGCAAAAAAAAAAAAAA

02730 prephenate dehydratase

390aa

MAPFVIRSLVNLPGQIAVKHLPTDQFPRIEIKLPLILVKPRHNTIVLASLHGENERAIE
ADGKNTQTALQLQDSPYDVVSRDALPRPLSSSQSSSSVSDGSRLRVAYQGVRGAYSE
SAAEKAYPNCEAVPCEQFDAAFEAVERWLVDRAVLPIENSLGGSIHRNYDLLLRHRL
HIVGEVKYAVRHCLLANHGVKVEDLKRVLSHPQALAQCEHTLTSLGLVREAVDDTA
GAAKHVALHKLKDTGAVASSVAAKIYGLNILAEDIQDDCDNVTRFLMLAREPIIPGTD
RPFKTSIVFSLEEGPGVLFKALAVFALRQINLTKIESRPLRNQPLRASDDSDNGFPKY
FDYLFYVDFEASMADQNAQNALKHLKEFATFLRVLGSYPVDTSMI

FIG. 4

PD 04020 prephenate dehydratase

1 – 1760bp ORF : 199 – 1485bp

AACACACACCAAAGACGGGAAACGGAGATATAGACTCACTATAGGGAATCCTTAGA
TTTGAGCTTGACGTCCCTTCTGTAGAGAACACCAAGCTGAAAACAAAAACATCTCC
TATCATCTCTATTTTTTTTTTCTTTTTTTAGTTTTCGTTTCTTCTTTCTCTTATTAGAT
TTAAGCACAACAAGAACATAAACAACTATGATGCAGGCTATCTCCCCTCCATCTCCC
CTCAAGTTATTAGTCCCAACTCGGCCTCGACTCGCTCCAGTCACCCCCAATAAACT
CATTCTTCATTGCATCTATCGATCGGATTCTGTCCAATTGCCTAATGGAGTTGGCTC
CAGTCGAGCTGATTGGCAAAGCTCTTGCGCCATATTAGCGAGCAAAGTCGTTTCCC
AAGAGCAACCTACTGATAAATCTAGTGAAGATTCACGTGGTGCTGATCATGTTGCT
GCTGTGAACGGGCACAAGGCCTCTATTGATCTTGGTTTAGTCCCTCTTAACAAAGG
TTCTAGTGATGGCGACTCCAATAACAAAAAGCCAACAAAGTCGTTAAGTATCACCG
ACCTCTCACCGGCTCCTATGCACGGCTCTCAGCTCCGTGTTGCTTATCAAGGGGTT
CCCGGCGCATATTCGGAGGCTGCAGCAGGAAAAGCTTATCCAAACTGTGAAGCCAT
CCCATGTGATCAATTTGACGTGGTTTTCCAGGCGGTGGAGCTTTGGATAGCAGATC
GTGCAGTTTTACCAGCTGAGAATTCTCTAGGTGGATCAATTCATAGAAATTATGATT
TGCTCCTTCGCCACAACCTCCACATCGTCGGTGAAGTACAATTTCCAGTCCACCAT
TGTCTCTTAGCCCTACCCGGTGTCCGTAAGGAGTATATTACTCGAGTGATCTCTCAC
CCTCAAGCACTTGCACAATGTGAGCTAACGCTCACTGAACTCGGGCTGCATGCTGT
CCGGGAGGCAGTAGATGACACGGCTGGCGCTGCAGAGTACATAGCCTCTAACAAT
CTCCGCAACACGGCAGCCATAGCCAGTGCACGCGCGGCAGAGCTGTACGGACTGC
AAATACTAGCCGATGGTATCCAGGACGATAAAAGCAACGTTACGCGATTCTTGATG
TTGGCTCGTGAGCCAATAATCCCTCGCACGGACCGTCCATTCAAGACAAGCATCGT
GTTCGCACACGATAAGGGGACGAGCGTGCTTTTCAAGGTGCTATCAGCGTTCGCAT
TCCGTAACATCAACTTGACGAAGATCGAGTCACGGCCACACCGAGATTGCCCGATC
AGGCTAGTGGACGATGCAAGTGCCGGGACGGCAAAGCACTTTGAGTACATGTTTTA
CTTGGATTTTGAAGCGTCGATGGCAGAAGTTAGGGCACAGAATGCATTGGCAGAG
GTGCAGGAGTTCACTTCTTTCTTAAGGGTGTTGGGGAGCTATCCTATGGACATGAC
TCCTTGGTGCCCTTCAAGGAGTGATTGACAAAACCCACCAATAAAATATTACAAAA
AAAGCCCTTAAAAGTGTTATTATTTGCACAAGAAAGGGCTATTATTTTATTTCTTTTG
CAATCTTTTTTATATTAATTCAAAGTAAATATTAAAAATAGTTGTGGATGCAATGTCT
AAGAATGTGAATACCATTTGGTATACTCAATCCTTTCCTTAGTATGCTATGCCAAATT
ATTAGGGGCATTAATGTGTATGCATATTTTACTAATAAAAGTTTCAGGTTTTAGAAA
AAAAAAAAAAAA

04020 prephenate dehydratase

429aa

MMQAISPPSPLKLLVPTRPRLAPVTPNKLILHCIYRSDSVQLPNGVGSSRADWQSSC
AILASKVVSQEQPTDKSSEDSRGADHVAAVNGHKASIDLGLVPLNKGSSDGDSNNK
KPTKSLSITDLSPAPMHGSQLRVAYQGVPGAYSEAAAGKAYPNCEAIPCDQFDVVFQ
AVELWIADRAVLPAENSLGGSIHRNYDLLLRHNLHIVGEVQFPVHHCLLALPGVRKE
YITRVISHPQALAQCELTLTELGLHAVREAVDDTAGAAEYIASNNLRNTAAIASARAA
ELYGLQILADGIQDDKSNVTRFLMLAREPIIPRTDRPFKTSIVFAHDKGTSVLFKVLS
AFAFRNINLTKIESRPHRDCPIRLVDDASAGTAKHFEYMFYLDFEASMAEVRAQNAL
AEVQEFTSFLRVLGSYPMDMTPWCPSRSD

FIG. 6

HPPD

01387 p-hydroxyphenyl pyruvic acid dioxygenase

1 – 1631bp ORF : 47 – 1381bp

TGGTTCATTCATTCATTCACTTCCAAAGAGAGAGAGGAGAAAAACTATGGGCAAGG
AAAACGATAGCGTTCCATCGTCGGCGCCAGGCTTCAAGCTCCTAGGATTTTCTAAC
TTCGTCAGAACAAATCCTCGATCCGATCTTTTCAAGGTCAAGCGCTTTCACCACGT
GGAGTTCTGGTGCACTGATGCTACCAATACGGCTTGTCGCTTCTCCTGGGGACTTG
GAATGCCTTTCGTAGCTAAATCCGATCTTTCCACTGGCAACGTCACCCATGCTTCCT
ATCTACTTCGCTCCGGCGACCTCAGCTTCCTTTTTACCGCTCCCTACTCTCCTACTA
TTGCTTCCATGGAGAACTTTTCACACACTGCCACCGCATCTATCCCAACCTTCAGTC
ATGAAGCGTGCCGGAATTTCTCAGCTAAGCACGGACTTGGTGTTCGAGCCATCGCC
ATAGAAGTTGAGGACGCAGAAATCGCGTACAACACTAGCGTCGCGCGCGGCGCCT
TACCCATGGGCGGACCAATAACGCTCGATAATCGTGCCGTTGTTGCGGAAGTTCAT
TTATATGGGGATGTAGTTTTGCGATATATTAGTTACAAGAACTCAAACCCTAACCTT
AATGATTCTAGTCCCGATAGTTGGTTTCTGCCAAAATTTGAATCAGTAGATGAGGCT
TCATCGTTTCCTTTGGATTACGGGATTCGGCGATTGGACCATGCGGTTGGAAACGT
GCCGGAATTAGCTCCAGCGGTCTCTTACGTCAAGGAGTTCACCGGTTTCCATGAGT
TTGCGGAGTTCACGGCGGAGGATGTGGGGACTAGTGAGAGCGGATTGAACTCGTT
GGTTTTGGCGAATAATGAAGACACAGTTTTGCTGCCGCTGAATGAGCCGGTGTTTG
GCACCAAGAGGAAAAGCCAAATACAAACATACTTGGAGCACAATGAAGGAGCTGG
TCTGCAGCATTTGGCGCTTGTGAGTGAAGATATATTCAAGACCTTAAGGGAAATGC
GGCGGAGGAGCGGCGTTGGAGGATTTGACTTTATGCCGTCTCCGCCGCCAACATAT
TATCGGAATTTGAAGAACAGGGTAGGGGATGTTTTGACTGATGAGCAGATCAAGGA
GTGTGAGGAGTTGGGAATTTTGGTGGATAGGGATGATCAGGGGACCTTGCTCCAG
ATTTTCACTAAGCCTGTTGGCGATAGGCCAACCATCTTTATAGAGATAATTCAAAGG
GTAGGCTGCATGATAAAGGATGAGACGGGGAAAGAATACCAGAAGGGTGGATGCG
GAGGTTTTGGGAAGGGAAACTTTTCAGAGCTATTCAAGTCTATTGAGGAATACGAG
AAGACACTTGAAGCCAAACGAAATGCAGAAGCCCGCTAAGGCATGAATATGAACTT
GGAATGCCATCAACCGTTACCACNTCACTGAAATAGTGTAGCCATGCTATTTAAATA
ACAGTGAAACTGAAAAGATAGAATAAGATGATAGGAAACTTTGTGGTTGTTGGCTG
TGTAAAACTTAATAAGATTAGAAGCTACTTGTTTGTTGCCTGTGTAAACTCACTAAT
TGATGAAAATAATTTAGCTAATGATAATATATTGTTGAAGGTGCGAAAAAAAAAAAA
AAA

FIG. 7

HPPD

01387 p-hydroxyphenyl pyruvic acid dioxygenase

445aa

MGKENDSVPSSAPGFKLLGFSNFVRTNPRSDLFKVKRFHHVEFWCTDATNTACRFS
WGLGMPFVAKSDLSTGNVTHASYLLRSGDLSFLFTAPYSPTIASMENFSHTATASIPT
FSHEACRNFSAKHGLGVRAIAIEVEDAEIAYNTSVARGALPMGGPITLDNRAVVAEV
HLYGDVVLRYISYKNSNPNLNDSSPDSWFLPKFESVDEASSFPLDYGIRRLDHAVGN
VPELAPAVSYVKEFTGFHEFAEFTAEDVGTSESGLNSLVLANNEDTVLLPLNEPVFG
TKRKSQIQTYLEHNEGAGLQHLALVSEDIFKTLREMRRRSGVGGFDFMPSPPPTYY
RNLKNRVGDVLTDEQIKECEELGILVDRDDQGTLLQIFTKPVGDRPTIFIEIIQRVGC
MIKDETGKEYQKGGCGGFGKGNFSELFKSIEEYEKTLEAKRNAEAR

FIG. 8

GGDR

09384 geranylgeranyl reductase

1 – 1793bp ORF : 12 – 1424bp

TGAAGACCAGAATGACTTCCTCCATCGCCTTCAAGTCCTTCACCGGACTCCGCCAT
TCCTCGGCTGAACCTCCCAAACTTCATTCCCAGTTACACAACATTTCCCCTCCCAAC
TATTGCCAGCGCCACCTTCAGATAACCGCTGGCATATCCAGTCCCAAGCTCCAGAA
CCGCAACCTCAGAGTAGCAGTCATCGGCGGTGGCCCCGCCGGTGGCGCAGCCGCC
GAGACCCTTGCTAAAGGTGGCATTGAGACTTACCTCATCGAACGCAAGCTCGACAA
CTGCAAACCATGCGGCGGAGCAATTCCTCTTTGCATGGTGGGCGAGTTTGACTTGC
CATTAGACATCATAGACCGCAAGGTGACCAAGATGAAGATGATCTCCCCTTCCAAC
ATCGCCGTGGACATTGGGCAAACTCTGAAGCCCCACGAGTACATTGGGATGGTGA
GACGCGAGGTGCTTGATTCTTACTTGAGAGAGAGAGCGGCGAGTAATGGGGCCAA
TGTCATCAATGGTTTGTTCTTGAAAATGGACCTTCCAAAGGGTGGTAAAGGCAGCG
AGACTGCACCTTATGTCCTCCATTACACGGAGTATAATGGAAAGGTAGGTGGGGCA
GGACAGAAGAAGACTCTGGAGGTTGATGCAGTAATTGGTGCTGATGGAGCCAATT
CCCGTGTTGCCAAGTCCATTGGTGCTGGTGATTATGACTACGCCATTGCTTTTCAG
GAGAGAATCAGAATCCCTGATGATAAAATGGTGTACTATGAGAACCTAGCTGAAAT
GTATGTCGGTGATGATGTATCTCCAGACTTTTATGGATGGGTGTTCCCCAAATGTGA
CCATGTTGCTGTTGGAACTGGCACAGTCACTCACAAAGGAGACATCAAGAAGTTCC
AATTAGCTACAAGAAATAGAGCCAAAGACAAGATCCTTGGGGGCAAGATTATTCGA
GTAGAGGCACACCCAATACCAGAACACCCGAGGCCACGCAGGTTATCAGACAGAG
TAGCACTAGTAGGGGATGCGGCAGGGTATGTGACGAAATGTTCAGGCGAGGGCAT
CTACTTTGCGGCGAAGAGTGGGAGAATGTGCGCGGAGGCAATCGTTGAGGGGTCA
GGGAATGGGAAGAGGATGGTGGATGAGAGTGACCTGAGGAAGTACTTGGAGAAAT
GGGACAAAACGTATTGGCCAACATACAAGGTGCTGGATGTGTTGCAGAAAGTATTC
TACAGATCGAACCCAGCAAGAGAGGCATTCGTGGAGATGTGTGCAGATGAGTATGT
GCAGAAAATGACTTTCGATAGCTATTTGTACAAGAAGGTGGTACCCGGGAATCCTT
TGGACGATTTGAAGTTGGCTTTCAATACCATTGGGAGCTTGGTGAGGGCTAATGCT
CTTAGAAAGGAGATGAACAAGCTTAGCGTATGAGCTACCTATGCTAAGATTTATGTG
TCTTTGTTCATTTATGTATTAATTAAATCTTAGCTAGCATATATGCTAAGATTTAAAAA
TTTAGCTACGATATTTATGTGTCTTTTGTTCTTGCTGTTAAAAATATGATAGCTAAAG
AGGAAATGGGATGTTCAGATTGTTCATGTCTACAGAGAAGCAAGTGTTGTTGCAGA
CTGGCTTGCCAACAGTGCTTTTTCTTTTGATCTTGGCCCTCACATACTGGTTTCTCC
AGCTGGGTCGACTGCTTTTTCAAGATGCCTCTGGTTTTGCTCAGTGCAGAGACGTG
CTGATGCTTCCTTGGTTTGAGTTTGTCTTGTTCCTTTAACCAAAAAAAAAAAAAAA

FIG. 9

GGDR
09384 geranylgeranyl reductase
471aa
MTSSIAFKSFTGLRHSSAEPPKLHSQLHNISPPNYCQRHLQITAGISSPKLQNRNLRV
AVIGGGPAGGAAAETLAKGGIETYLIERKLDNCKPCGGAIPLCMVGEFDLPLDIIDRK
VTKMKMISPSNIAVDIGQTLKPHEYIGMVRREVLDSYLRERAASNGANVINGLFLK
MDLPKGGKGSETAPYVLHYTEYNGKVGGAGQKKTLEVDAVIGADGANSRVAKSIGA
GDYDYAIAFQERIRIPDDKMVYYENLAEMYVGDDVSPDFYGWVFPKCDHVAVGTGT
VTHKGDIKKFQLATRNRAKDKILGGKIIRVEAHPIPEHPRPRRLSDRVALVGDAAGY
VTKCSGEGIYFAAKSGRMCAEAIVEGSGNGKRMVDESDLRKYLEKWDKTYWPTYK
VLDVLQKVFYRSNPAREAFVEMCADEYVQKMTFDSYLYKKVVPGNPLDDLKLAFN
TIGSLVRANALRKEMNKLSV

FIG. 10

HPT

07558 homogentisic acid phytyl transferase

1 – 1563bp ORF : 93 – 1334bp

GAACACAGAAAGAGAGATTAGTAGTAGCAGTAGTTTTGGACTTCTGATTAACTTAA
GAAGCATCAGTTCCTAATCAGTTGGAGATGGTGGTTATGGAGTCTCTGCTTCTTGG
GTCGTTTCCTAAGCCTTCTTCGGTCACTTCTGGTGGAAATTGTTGGGAGAGTAAAA
ATTTCAGAGTGGGTCACTCTCCAAGGGTAACCCGTTCTATAGCATCAGTCAGAGTT
GCCAGGTGCAGAACATGGAACGTCCTAGAAAGATATTATGTTGCAAAGTTTCCGCT
TCCTCGAATGAACCATCATCTTAGATGTAGTGTGGAAAGATCTAACATTTATCAGAG
AAAAAAGGGTGCCCATTTCTTGGTGTATACCGCCTCTGGACAGCCTCTTGAATCTG
AGTCAGATGCTTATAGTCCTAAGATTACTTCAAATTCTGTTCTCAATGCATTAGATG
CTTTCTACAGATTTTCACGTCCTCATACGGTTATAGGCACAGCTTTGAGCATCTTAT
CGGTTTCTCTCCTTGCAGTAGAGAAACTCTCGGATCTTTCTCCACTGTTCTTGACA
GGTGTTTTGGAGGCAGTGGTTGCTGCCCTCATGATGAATGTATACATAGTTGGTTT
AAATCAATTAACTGACATCGAAATAGACCAAGTTAACAAGCCATATCTTCCATTGGC
ATCTGGAGAGTATTCCAAGGGCATTGGTGTTCTGAATGTGGCATCTTTCTCCATAAT
GAGCTTTTGGCTTGGATGGGTTGTTGGTTCATGGCCATTGTTTTGGGCTCTTTTTG
TCAGTTTTGTTCTTGGAACAGCATATTCAATCAATTTGCCATTATTGAGATGGAAAA
GGTTTGCATTTGTTGCAGCAATGTGCATCTTAGTTGTCCGGGCAGTGATCGTTCAA
CTTGCCTTTTATCTGCACATGCAGACCCACGTGTACAGAAGACCTACTGTCTTTTCC
AGGCCTCTGATTTTTGCAACTGCATTCATGTGCTTATTCTCTGTTGTTATAGCATTAT
TCAAGGATATACCTGATATTGAAGGGGATAAGATATTTGGTATCCGATCCTTTACAG
TGCGCTTGGGCCAAGAACGGGTTTTCTGGACCTGTATTTCTCTGCTTGAAATAGCT
TATGGTGTTGCTATTTTAGTTGGAGCAGCTTCTTCCCACACCTGGAGCAAGTGTATC
ACGGTTCTGGGGCATGCCATATTGGCTTCAATACTGTGGAACCGTGCTAAAGCTGT
TGATCTCAAGAGCAAAGCTGCTATAACTTCATGTTACATGTTTATTTGGAAGCTCTT
TTATGCAGAATACTTGCTCATACCACTCGTAAGATGAGCATGCAAAGCATTGTGGA
GAGAAGGAAACTGCAGCCGTCTCTAAAAATGGAGTATTCTACTGAAACATTAATGC
CTAGAAAGAGGATACTATGGTTTGCTTGCAAGTTCTGTATGCCTATCATTTATCTCG
AACAATTGTAATGCTGGGAGAAAAAAATGCAATTACTATGTAATGGCATTGTATTAG
TACACAATTTATTATTTGCATTTAAAAAAAAAAAAAA

FIG. 11

HPT

07558 homogentisic acid phytyl transferase

414aa

MESLLLGSFPKPSSVTSGGNCWESKNFRVGHSPRVTRSIASVRVARCRTWNVLERY
YVAKFPLPRMNHHLRCSVERSNIYQRKKGAHFLVYTASGQPLESESDAYSPKITSNS
VLNALDAFYRFSRPHTVIGTALSILSVSLLAVEKLSDLSPLFLTGVLEAVVAALMMNV
YIVGLNQLTDIEIDQVNKPYLPLASGEYSKGIGVLNVASFSIMSFWLGWVVGSWPLF
WALFVSFVLGTAYSINLPLLRWKRFAFVAAMCILVVRAVIVQLAFYLHMQTHVYRRP
TVFSRPLIFATAFMCLFSVVIALFKDIPDIEGDKIFGIRSFTVRLGQERVFWTCISLLEI
AYGVAILVGAASSHTWSKCITVLGHAILASILWNRAKAVDLKSKAAITSCYMFIWKLF
YAEYLLIPLVR

FIG. 12

MGGBQMT

05400 2-methyl-6-geranylgeranyl benzoquinone methyl transferase

1 – 1410bp    ORF : 165 – 1187bp

GATTTGACCGGCACTTTGCTATTCTAGCCGCCACATCATGCTTACTGAATAATCACA
AACCACCGCCACTGCCGATTAATAAGCTGGTGTCTGCAAGTGGGTTTCCTTTGAAA
TCTTCAAATTCACTTGTTCTCCTTGGTGGGTAATCTTTGGTTCATCCATTCATGGCT
TCCTCAATGCTTAGTGGAGCTGAGAACCTCACTCTCATGAAAGGCATAAGCCCAAA
AGTGAAAGGGTTAGGTTTTTCGCGGTCAGATTTTCACGGGAACCACTTTCCCGGAG
TGACAATTACTTGCTCTAGAATCTTCAGGACAAGAACAATGATGCCCAAGTGCAGT
TTATCAGCCTCTAGGCCAGCTTCTCAGCCCAAGTTCATCCAACACAAGAAAGAGGC
TTTTTGGTTCTACAGATTCCTCTCAGTTGTATATGACCATATTATAAATCCTGGTCAC
TGGACTGAGGACATGAGAGATGATGCACTAGAGCCTGCTGATCTCAGTGACAGGA
ATATGGTAGTTGTAGATGTGGGCGGTGGTACTGGTTTCACTACTTTGGGTATAGTG
AAGCATGTGGATGCCAAAAATGTCACCATTCTTGATCAGTCCCCGCATCAGCTTGC
AAAGGCCAAGCAGAAGGAGCCCTTGAAGGAGTGTAAGATTATTGAGGGCGACGCA
GAGGATCTGCCATTTCCTACCGATTATGCTGACAGATATGTGTCCGCTGGGAGTATT
GAGTATTGGCCAGATCCACAACGTGGCATCAAGGAAGCATACAGGGTCCTGAAACA
CGGAGGAAAAGCCTGCTTAATTGGTCCAGTGCATCCAACATTTTGGTTGTCTCGTT
TCTTTGCAGATGTTTGGATGCTTTTCCCAAAGGAGGAAGAGTACATTGAATGGTTT
GAAAAGGCTGGGTTTAAGGATGTCCAACTGAAGCGTATAGGCCCAAAATGGTATCG
TGGTGTTCGCCGGCATGGGCTGATCATGGGATGTTCTGTGACAGGTGTTAAACCTG
CATATGGAGATTCTCCTTTACAGCTTGGTCCAAAGCAAGAGGACGTGGCAAAGCCG
GTGAACCCATTTGTGTTCCTTCTGCGTTTTATTTTGGGTGCCATGGCAGCAACATAC
TATGTACTGGTGCCTATCTACATGTGGCTCAAAGATCAAATTGTACCCGAAGGTAGA
CCAATCTAAGAGGGATTATGGAGTTGCTTTTGTGGGCTGCTTCTTCTTCTTCTTCTT
ATTTATTTTTTTTTTATTTTTTTAAAGTTTCCACCTGTGTGGTCATTAGAACGAGTAT
GCAAGACTAGGTGAGATCAGTGTATCATTGAACACTTCTAAGACTTTTTCTAAAGTT
TCTTTTGAAATAATAATAGAAGCTGAAAGTCGTCATTGGAACGAAAAAAAAAAAAA
A

FIG. 13

MGGBQMT

05400 2-methyl-6-geranylgeranyl benzoquinone methyl transferase

341aa

MASSMLSGAENLTLMKGISPKVKGLGFSRSDFHGNHFPGVTITCSRIFRTRTMMPK
CSLSASRPASQPKFIQHKKEAFWFYRFLSVVYDHIINPGHWTEDMRDDALEPADLS
DRNMVVVDVGGGTGFTTLGIVKHVDAKNVTILDQSPHQLAKAKQKEPLKECKIIEG
DAEDLPFPTDYADRYVSAGSIEYWPDPQRGIKEAYRVLKHGGKACLIGPVHPTFWLS
RFFADVWMLFPKEEEYIEWFEKAGFKDVQLKRIGPKWYRGVRRHGLIMGCSVTGV
KPAYGDSPLQLGPKQEDVAKPVNPFVFLLRFILGAMAATYYVLVPIYMWLKDQIVPE
GRPI

FIG. 14

HGGT homogentisic acid geranylgeranyl transferase

1 - 1837bp ORF : 82 - 1317bp

TTATAAAGATTCTGATAAAACAATTCTGTAAATTGCAGATCGCTAGAGACTCAGAGAGA
GAGAGAGAGAGAGAGGTACACTATGCTTCATTACTATCCAAGCCCATGCCTCAACACC
CCTCCAAAGTATCAAGTCCTTGATCCAGGTCAAGTTACAACAGTAACAGTGTTAAAGA
AACAAGTAAATCACATCCTGAAAGAAAGCCAGTGCAAGAAGCCCATAATTTGTTCCTT
AAGATCGTTATCTTGGGCCAAAAATAGCAGGAAAAAAGAGTTATATGTGTTGAGAAAT
CTACGTATACTAACTAGAAAGAATGGTATTCCTGCCATTTTTTTACAGAATAATTGGCTT
GCACCAAATTCTGAGGATGGTGATGATATTTGTTCAAGTTCTAAGAGGGGACCAATTCT
AGAGCACTTAAATTCCTTATATCAGTTTTCACGTCCTCACACTGTGATTGGCACTATTA
TAGGAATAACATCAGTTTCCCTTCTTCCGGTAGAAACAATTGTTGACCTGTCTCCCACA
TATTTTATTGGGCTACTGAAAGCACTGGTGCCTTCAGTGTTGATGAACATTTACGTGGT
GGGATTGAATCAATTGTTTGATGTTGAAATTGACAAGGTAAATAAACCCTATCTCCCAC
TTGCTTCTGGCAAGTTCTCAATGGCAACTGGTATCCTAATTGTTTCTGCATCTTTATTG
CTGAGTCTTTATATGGGAATTACGTTTCAATCTCCACCACTTCTTGCAGCCCTCCTTAT
AAGTTTTGCCCTTGGAAGTGTATATTCCATTGAACTTCCCTTTCTGAGATGGAAGAAAC
ATGCTTTTCTTGCTGCAAGTTGTATTCTGATCGTAAGAGCAATGGTTGTTCAACTTGCC
TTCTTTGTACACATCCAGAAATTTGTTCTTGGAAAATCCATATTTATTCCCAGATCGTT
GATGTTTGCAACTGCTTTCATGTGCTTCTTCTCTGCTGCTATTGCACTATTCAAGGACA
TCCCAGATGTGGAGGGGGACAGAGATTATGGGATCCAATCCTTCAGTGTCAGCCTTGG
CCAAGAAAGAGTCCTTTGGCTTTGCGTTAACATGCTATTAGTGGCCTATGGTGCTGCT
GTCGTACACGGAGCTTCTTCTCCTTCTTCGCTCCTACCAGTCAAGCTTATCACAATGAT
AGGGCATAGCACAATTGCTTGGATTTTGTGGATGAAAGCACAATTCGTTGATCTCACC
AGCCAGAAGTCTATTACTTCTTTTTACATGTTCATATGGAAGTTATTCTATGCGGAGTAT
TTCCTTATCCCTTTTGTGCGTTGAGAGTGACAAATATTAAAGGCTTGCAACTTCAAGAA
GACAATAACGTCCCCCAGGAACCACTGTTATAACACAGATGAAAGAGATTGAGGCATT
GCTGGCTGGTTTCGGTTTTTTTTTTTTTTTTTTTTTTTTTAATAAGCAATAAGTTAATTT
TATTAATAAAAAGTAGGGCAAGAAAAATTTAGCATGAGACACTTAGCTAAACCCCGACC
TGGCCAACAAGCCTCTCCTTAGAACCCAAATTAAGAGGAGCATGCCAAGCGAAGACAT
TGTTGGGTTATCACTCATGGGATTAGCAAAAATATATTTATGCAAAGGTGGTTTACCA
AGAGGAACACTGCAGGTGATGGTGGAGGACAAGACAAACACTCCACTTCTATAGAAAA
TATTAATGGAAACACCTGCCTAAGAAAATTTACCAATTCAATTGGTGAGTGCAAAGAA
CCTTAAGTGCTTTGTATTTTTGGCTAATAAATGATTGCTACATATACTATTAGTATCAGA
AAAAAAAAAAAAAA

FIG. 15

HGGT
homogentisic acid geranylgeranyl transferase
411a
MLHYYPSPCLNTPPKYQVLDPGQVTTVTVLKKQVNHILKESQCKKPIICSLRSLSWAKN
SRKKELYVLRNLRILTRKNGIPAIFLQNNWLAPNSEDGDDICSSSKRGPILEHLNSLYQF
SRPHTVIGTIIGITSVSLLPVETIVDLSPTYFIGLLKALVPSVLMNIYVVGLNQLFDVEIDK
VNKPYLPLASGKFSMATGILIVSASLLLSLYMGITFQSPPLLAALLISFALGSVYSIELPFL
RWKKHAFLAASCILIVRAMVVQLAFFVHIQKFVLGKSIFIPRSLMFATAFMCFFSAAIAL
FKDIPDVEGDRDYGIQSFSVSLGQERVLWLCVNMLLVAYGAAVVHGASSPSSLLPVKLIT
MIGHSTIAWILWMKAQFVDLTSQKSITSFYMFIWKLFYAEYFLIPFVR

FIG. 16

MPBQMT
    2-methyl-6-phytyl benzoquinone methyl transferase
1 – 1282bp      ORF : 84 – 1106bp GAGTGGAGTCTGCAACTGGGTTTTCTTTACAACCTCCAGATTGACTTGTTTTCCTTGGTG
GGTAATCTTTGATTCATCTAGTCATGGCCTCCTTAATGCTCAATGGAGCTGAGAACTTCAC
TCTCATGAGCGGCATAACCCCAAAAGGGTTAGGTTTTTTGGGTTCGGATTTTCATGGGAA
CCACTTTCCTAGAGTGAATTTAATCAGTAGCTCTAGAATCTCCAGGACAAGAACAGTGAT
GCCCAAGTGCAATTTATCAGCCTCTAGGCCAGCTTCTCAGCCCAGGTTCATCCAACACAA
GAAAGAGGCTTTTTGGTTCTACCGGTTCCTGTCAATTGTATATGATCATGTGATAAATCCT
GGGCACTGGACTGAGGACATGAGAGACGATGCGCTAGAGCCTGCGGATCTCAATAACAG
GAATTTGCTAGTTGTAGATGTTGGCGGTGGCACCGGTTTCACTACTTTGGGTATTGTAAA
GCATGTGGATGCCCAAAATGTTACCATTCTTGATCAGTCCCCGCATCAGCTTGCAAAGGC
CAAGCAGAAGGAGCCCTTAAAGGATTGTAAGATAATTGAGGGCGACGCAGAGGATCTGC
CATTTCCTACTGATTATGCGGACAGATATGTGTCCGCTGGGAGTATTGAGTACTGGCCAG
ACCCACAACGTGGCATCAAGGAAGCATACAGGGTCCTGAAACTAGGAGGAAAAGCCTGC
TTAATTGGTCCAGTATATCCAACATTTTGGTTGTCTCGCTTCTTTGCAGATGTATGGATGC
TCTTCCCAAAGGAAGAAGAGTACATTGAATGGTTTGAAAAGGCTGGGTTTAAGGATGTTC
AACTGAAGCGTATTGGCCCAAAATGGTATCGTGGTGTTCGCCGGCATGGGCTAATCATGG
GATGTTCTGTGACAGGGGTTAAACCTGCATCTGGAGATTCTCCTTTAAAGCTTGGTCCAA
AGGAAGAGGACATAGCAAAGCCAGTGAACCCATTTGTGTTCCTTCTGCGTTTTATTTTGG
GTGGCTTGGCGGCAGCGTACTATGTGCTGGTGCCTATCTACATGTGGCTTAAAGATCAAA
TTGTACCCAAGGGTAGACCAATCTGAGACTAAAAGGGATTTTTAGAGTTCCTTAAGTGGG
CCATTTTATTTTTAATTTATAGACAATTTCCTCCTGTGTGGGCACACAAGTAAATTAGACAT
ATGCTTTTAATTAGATGCCTCTCCTTTGATTTTTCTAATTCTAGTTGTGAAATTCATTTTTC
AAAACAAAAAAAAAAAAA

FIG. 17

MPBQMT 2-methyl-6-phytyl benzoquinone methyl transferase

340aa

MASLMLNGAENFTLMSGITPKGLGFLGSDFHGNHFPRVNLISSSRISRTRTVMPKC
NLSASRPASQPRFIQHKKEAFWFYRFLSIVYDHVINPGHWTEDMRDDALEPADLNN
RNLLVVDVGGGTGFTTLGIVKHVDAQNVTILDQSPHQLAKAKQKEPLKDCKIIEGD
AEDLPFPTDYADRYVSAGSIEYWPDPQRGIKEAYRVLKLGGKACLIGPVYPTFWLSR
FFADVWMLFPKEEEYIEWFEKAGFKDVQLKRIGPKWYRGVRRHGLIMGCSVTGVK
PASGDSPLKLGPKEEDIAKPVNPFVFLLRFILGGLAAAYYVLVPIYMWLKDQIVPKGR
PI

FIG. 18

TC tocopherol cyclase

1 – 2008bp    ORF : 123 – 1649bp

TCATATAAAATATTTTTTCTAAGGATCGCTTAAAACATTTTCCATGAAATTTTCGGTTTTCT
TCTAAAAGTTTTATAGAATTTAAGCGCAGTTATCTACTGTTAATTTTCTGTAATCCAACAAT
GGAAGCTAACTTCCAATGCTCGCTCTACCATCTTCACCATTTCTCTTCCAATATGGGATTT
CCTGCTCTAAACCCTTGTTCCACCCTTAAACCTTTCCGTTTGAATCAAAGCTCCGTCGGA
ATTCATTGGCGGTCACTGCAAGTAGGGTTTCGATCATCGAGGTCCCGACTCTTGGTTTCC
AATTCGGTGACTGACCGTCAAACTTCGACTGTTGAAAGAGGAGGTACTGAGGGTGTGGC
CTCTGCAAGTCCCGTTTATGTCGCCACTCCTCCCAACCGTGAGCTTCGAACTCCTCACAG
CGGGTACCATTTTGATGGAACCACGCGGCAATTTTTTGAGGGTTGGTACTTCAAGGTCTC
TATTCCTGAGCGGAAGGAGAGCTTTTGTTTCATGTATTCTGTGGAGAATCCAGCATTTCG
GAAGAAATTGTCGCCCTTGGAAGTGGCACAGCATGGACCCAGATCCACTGGAGTTGGTG
CTCAAATTCTCGGGGCTTCTGACAAGTATATATGTCAATATTCTGAAGAATCTCAGAACTT
CTGGGGAAGTAGGCATGAACTGATGTTGGGGAATACTTTTGTGGCCGAGAAAGGCATGC
AGCCTCCATCCAAGGAGGTTCCTCCTCAGGAGTTTAATAGAATGGTTTCAGAAGGTTTTC
AAGTCACCCCATTATGGAATCAAGGTTTTATTCGTGATGATGGCAGGTCAGATTATGTGA
AAACTGTGAAAACTGCACGTTGGGAGTACAGTACTCGCCCTGTTTATGGATGGGGTAATG
TGGGATCCAAACAACAGTCCACTGCAGGCTGGCTTGCTGCATTTCCTGTATTTGAACCCC
ATTGGCAAATATGCATGGCAGCCGGACTTTCAACAGGCTGGATAGAGTGGGATGGTGAA
AGATTTGAGTTCAAAGATGCACCTTCTTACTCAGAAAAGAACTGGGGTGGAGGCTTTCCA
AGGAAATGGTTTTGGGCTCAGTGTAATACCTTTGAAGGTGCAAGCGGAGAAGTTGCTTT
GACTGTGGGTGGTGGGCTGAGGCAATTGCCTGGACTAACTGAGACCTTTGAAAATGCTG
CGTTGATTGGAGTGCATTATGATGGAATTTTCTATGAATTTGTACCATGGAAAGGTGTTGT
AACTTGGGAAATCAGCCCATGGGGTTACTGGTTCGTAACTGCAGAGAATGAGACACATTT
GGTTGAATTGGAGGCAACAACAAAGGATCCGGGAACAACACTTCGTGCTCCAACAACAG
AGGCTGGCCTTGCTCCAGCTTGCAAAGATACTTGTTATGGTGTTCTGAAATTGAAATTAT
GGGAACGAAGATATGATGGCTCTAAGGGCAAGATAATTTTGGATGTTACAAGTGACATGG
CAGCAGTAGAAGTTGGTGGAGGACCGTGGTTTAACACCTGGAAAGGGAAGACAACTACG
CCAGAGCTTCTCAGCCGTGCTCTGAGAGTGCCCTTAGACGTGGATGGGATCTTCAATTTT
CTTCCACTATTCAAACCCCCTGGCTTATAGGCAGTTGGTTCAGGTCTTTCATTGCACCAAA
TCGATATCTTTGCAACTGGAGAAGTAAGATCTGGCCAGTGTGGCATGACATGGTCCGTCT
ATATTTCCGTAGGTGGAATCTTATGAACATTTCATGGCAGCACCAACCTGTACTTGATCGC
CTTTTTCCATGTCTGTTCATCACTTTTATCACTCAGACAATTCTCGATAGCTCCATAGACA
TTTGATACATTCTTGCAAATTTTATGAGGAGTCGGTATATGATATGCTTTGAAATGATATTG
AAAATTTACTTTATGCCTGAGAGCCGGTAAAAGGAGCTCAAATACTAGGATGCAAGTGCT
CAAATTCAGACAAAAAAAAAAAAA

FIG. 19

TC
tocopherol cyclase
508aa
MEANFQCSLYHLHHFSSNMGFPALNPCSTLKPFRLNQSSVGIHWRSLQVGFRSSRS
RLLVSNSVTDRQTSTVERGGTEGVASASPVYVATPPNRELRTPHSGYHFDGTTRQFF
EGWYFKVSIPERKESFCFMYSVENPAFRKKLSPLEVAQHGPRSTGVGAQILGASDKY
ICQYSEESQNFWGSRHELMLGNTFVAEKGMQPPSKEVPPQEFNRMVSEGFQVTPL
WNQGFIRDDGRSDYVKTVKTARWEYSTRPVYGWGNVGSKQQSTAGWLAAFPVFEP
HWQICMAAGLSTGWIEWDGERFEFKDAPSYSEKNWGGGFPRKWFWAQCNTFEGA
SGEVALTVGGGLRQLPGLTETFENAALIGVHYDGIFYEFVPWKGVVTWEISPWGYW
FVTAENETHLVELEATTKDPGTTLRAPTTEAGLAPACKDTCYGVLKLKLWERRYDG
SKGKIILDVTSDMAAVEVGGGPWFNTWKGKTTTPELLSRALRVPLDVDGIFNFLPLF
KPPGL

FIG. 20

γ-TMT

γ-tocopherol methyl transferase

1 – 1408bp ORF : 82 – 1125bp

AAGTGCCATTACGCTACCCCATAGCACAGTGTTCCACCGTTCGGTTATCCCCCACAGTTT
CTGTCATCTCCAGCTCTCTCCATGTTGCTGCAGTGCTACTTATATCCGCCCTCAATCCTCC
CACAACTCCGCACAAATCTTCAATCCTCGCTATTTCTTCCTACTCGTTGTCGTACTTCTCA
CGCTCCGCTGCTCCGTTCGATCACCGTCAAGGCTTCAATATCTACTGTCATGGACGCTGA
CGCTCAAGTGACCTTGCTAAAGAAAGGCATAGCTGAACTGTATGACGAGTCATCTGGTAT
ATGGGAAGCCTTATGGGGAGACCACATGCACCACGGGTTCTACGACACGGATGTTAAAG
TTTCGGGCTCTCTTTCCGATCATAGAGCTGCTCAGATCCGAATGATCGAGGAGGCTCTCA
GGTTCGGCAGCGTTCCAGAGGACCCAAAAAAGTGGCCTAAGAACGTGGTTGATGTTGGC
TGTGGGATTGGAGGCAGCTCTAGGTACCTGGCAAAGAAATTTGGGGCTCATTGCCAAGG
CATTTCTCTCAGTCCTTTCCAAGTCCAGAGGGCCAATTCTCTAGCAGCTGCTGACGGACT
GGCTGACAAGGCTTCCTTCCAAGTTGCAGATGCTTTAGACCAACCATTTCCAGATGGGCA
GTTTGATCTGGTCTGGTCAATGGAGAGTGGAGAACATATGCCTGACAAAAGAAAGTTTGT
TAGTGAGTTGGCTAGAGTTGCAGCCCCAGGAGCCAGAATTATTATAGTAACATGGTGCCA
TAGGAACCTCAGCCCTTCTGAAGAATCTTTGCAGACATGGGAGAAAGCACATCTGAAGA
AGATATGTGACGCTTATTATCTTCCTGAATGGTGTTCTGCTGCTGATTATGTTGAAATGCT
CGAGTCTCTCTCTCTACAGGATATTAAAACAGCAGATTGGTCTCAGAATGTGGCCTCTTT
TTGGCCAGCAGTGATTCGCTCGGCATTGACTTGGAAGGGCTTGACTTCACTAGTGCGTA
GTGGTCTAAAAACTATTAGAGGAGCATTGGTGATGCCATTGATGATCCAAGGATACCAGA
AAGGTCTTATCAAGTTTGCCATCATTACATGTCGAAAGCCTGAATAAATTTATAGAAAGGT
TGAATGAACAACAGATTGCGCAGATATGGCAAAGATCAAAGGATTTGAATAAGGATGACA
CTCACTCTTTAGAAGTTTGAGATTAAGCTTATCATCATCATTACAAGTAAAATAATTGAAT
AAGGTATAGTGATTCCATTGATGATCCAACAAGGATACAAGAAAGACATATTATTAGAGAA
AAGGGAATTAAAAAATGGTGGGGAGGGGATATATTTGTCACATTATCTACAATGACAAATT
ATTTACAACCAAAAAAAAAAAAAAA

FIG. 21

γ-TMT

γ-tocopherol methyl transferase

347aa

MLLQCYLYPPSILPQLRTNLQSSLFLPTRCRTSHAPLLRSITVKASISTVMDADAQVT
LLKKGIAELYDESSGIWEALWGDHMHHGFYDTDVKVSGSLSDHRAAQIRMIEEALR
FGSVPEDPKKWPKNVVDVGCGIGGSSRYLAKKFGAHCQGISLSPFQVQRANSLAAA
DGLADKASFQVADALDQPFPDGQFDLVWSMESGEHMPDKRKFVSELARVAAPGAR
IIIVTWCHRNLSPSEESLQTWEKAHLKKICDAYYLPEWCSAADYVEMLESLSLQDIK
TADWSQNVASFWPAVIRSALTWKGLTSLVRSGLKTIRGALVMPLMIQGYQKGLIKFAI
ITCRKPE

SEQUENCE LISTING

<160> NUMBER OF SEQ ID NOS: 20

<210> SEQ ID NO 1
<211> LENGTH: 1677
<212> TYPE: DNA
<213> ORGANISM: Hevea brasiliensis

<400> SEQUENCE: 1

```
gacggcacaa agccaaccca ccttctgtaa aactatactt ccgtacttcg gacgtctagc     60
ctttttctcc ttttctcacc gcctccactt tcctcagact ttacaaatat ccctctctct    120
ctctctctct ctctctcatg caccttgcct aactcatcaa tggcgccttt tgttatacgg    180
tctcttgtta accttccggg ccaaatcgcc gttaaacact tgccaactga tcaatttccc    240
agaattgaaa tcaaattgcc gctgattttg gttaaaccgc gacataatac gattgttttg    300
gcctctcttc atggagaaaa cgagagagca atcgaggctg acgggaagaa cactcagact    360
gctcttcaat tgcaggattc tccttacgac gtcgtttcca gagatgcgct cccgaggccg    420
ttatcttctt ctcaatcctc cagttcggtc tctgatgggt cacgtcttcg cgttgcttac    480
cagggagttc gtggcgcgta cagcgaatca gcggccgaga aagcctatcc gaattgcgaa    540
gcagtaccgt gtgagcaatt tgacgcggct tttgaggctg ttgaacgatg gcttgtggac    600
agagcagttt tgcccattga gaattcctta ggtgggagca tccacagaaa ttatgacctt    660
ttgctccgtc atagactgca tatagtaggg gaagtgaaat atgctgttcg ccattgctta    720
ctagccaatc atggtgttaa agttgaagac ttgaagaggg tcctaagtca tccgcaggcc    780
cttgctcaat gtgagcatac attaacaagt ttgggattgg ttagagaagc agtggatgat    840
actgctggtg cagcaaagca tgttgcactt cacaaactga aagacacagg agctgttgct    900
agttctgtgg ctgcaaagat ttatgggttg aatatattag ctgaagatat tcaggatgat    960
tgtgataatg ttactcggtt tctgatgcta gccagggagc caataatccc aggaacggac   1020
aggccattca agacgagcat tgttttttca cttgaggagg gtcctggagt gcttttcaaa   1080
gcacttgctg tttttgcttt gcggcaaatc aaccttacta agattgagag tcgtccattg   1140
cggaaccagc ccttgagagc atctgatgat agcgacaatg ggtttccaaa atactttgac   1200
tatcttttct atgtggattt tgaggcatca atggccgacc agaatgcaca gaatgccctc   1260
aagcacctga aggagtttgc gactttctta cgagttttgg ggagttatcc agtggatact   1320
agcatgatat aaatgatcct ctaacacggg gcctggagga aaaaaattac cctgataaga   1380
acggaagcac tgatgatatt cctttttcaa atttatcact aaatggatgc agcaaaactt   1440
gatctatcgc catttcatcc aattttgtag tgtcttctca atactgcaca tgtaattaag   1500
agttaatcgg gtatttttat agaggttgtt atttctttcg tgcttggcaa tttttctgt   1560
gggttcactt acgtgtcacc aatgttgggc atgacatacc aaaatgctgt acaagagaag   1620
ttacaaattc aaattctttc tttcctttt agtgtttgat tgcaaaaaaa aaaaaaa      1677
```

<210> SEQ ID NO 2
<211> LENGTH: 390
<212> TYPE: PRT
<213> ORGANISM: Hevea brasiliensis

<400> SEQUENCE: 2

```
Met Ala Pro Phe Val Ile Arg Ser Leu Val Asn Leu Pro Gly Gln Ile
1               5                   10                  15

Ala Val Lys His Leu Pro Thr Asp Gln Phe Pro Arg Ile Glu Ile Lys
```

-continued

```
            20                  25                  30

Leu Pro Leu Ile Leu Val Lys Pro Arg His Asn Thr Ile Val Leu Ala
        35                  40                  45

Ser Leu His Gly Glu Asn Glu Arg Ala Ile Glu Ala Asp Gly Lys Asn
    50                  55                  60

Thr Gln Thr Ala Leu Gln Leu Gln Asp Ser Pro Tyr Asp Val Val Ser
65                  70                  75                  80

Arg Asp Ala Leu Pro Arg Pro Leu Ser Ser Ser Gln Ser Ser Ser Ser
                85                  90                  95

Val Ser Asp Gly Ser Arg Leu Arg Val Ala Tyr Gln Gly Val Arg Gly
            100                 105                 110

Ala Tyr Ser Glu Ser Ala Ala Glu Lys Ala Tyr Pro Asn Cys Glu Ala
        115                 120                 125

Val Pro Cys Glu Gln Phe Asp Ala Ala Phe Glu Ala Val Glu Arg Trp
    130                 135                 140

Leu Val Asp Arg Ala Val Leu Pro Ile Glu Asn Ser Leu Gly Gly Ser
145                 150                 155                 160

Ile His Arg Asn Tyr Asp Leu Leu Leu Arg His Arg Leu His Ile Val
                165                 170                 175

Gly Glu Val Lys Tyr Ala Val Arg His Cys Leu Leu Ala Asn His Gly
            180                 185                 190

Val Lys Val Glu Asp Leu Lys Arg Val Leu Ser His Pro Gln Ala Leu
        195                 200                 205

Ala Gln Cys Glu His Thr Leu Thr Ser Leu Gly Leu Val Arg Glu Ala
    210                 215                 220

Val Asp Asp Thr Ala Gly Ala Ala Lys His Val Ala Leu His Lys Leu
225                 230                 235                 240

Lys Asp Thr Gly Ala Val Ala Ser Ser Val Ala Ala Lys Ile Tyr Gly
                245                 250                 255

Leu Asn Ile Leu Ala Glu Asp Ile Gln Asp Asp Cys Asp Asn Val Thr
            260                 265                 270

Arg Phe Leu Met Leu Ala Arg Glu Pro Ile Ile Pro Gly Thr Asp Arg
        275                 280                 285

Pro Phe Lys Thr Ser Ile Val Phe Ser Leu Glu Glu Gly Pro Gly Val
    290                 295                 300

Leu Phe Lys Ala Leu Ala Val Phe Ala Leu Arg Gln Ile Asn Leu Thr
305                 310                 315                 320

Lys Ile Glu Ser Arg Pro Leu Arg Asn Gln Pro Leu Arg Ala Ser Asp
                325                 330                 335

Asp Ser Asp Asn Gly Phe Pro Lys Tyr Phe Asp Tyr Leu Phe Tyr Val
            340                 345                 350

Asp Phe Glu Ala Ser Met Ala Asp Gln Asn Ala Gln Asn Ala Leu Lys
        355                 360                 365

His Leu Lys Glu Phe Ala Thr Phe Leu Arg Val Leu Gly Ser Tyr Pro
    370                 375                 380

Val Asp Thr Ser Met Ile
385                 390
```

<210> SEQ ID NO 3
<211> LENGTH: 1760
<212> TYPE: DNA
<213> ORGANISM: Hevea brasiliensis

<400> SEQUENCE: 3
aacacacacc aaagacggga aacggagata tagactcact atagggaatc cttagatttg 60

-continued

```
agcttgacgt cccttctgta gagaacacca agctgaaaac aaaaacatct cctatcatct    120
ctattttttt tttctttttt tagttttcgt ttcttctttc tcttattaga tttaagcaca    180
acaagaacat aaacaactat gatgcaggct atctcccctc catctcccct caagttatta    240
gtcccaactc ggcctcgact cgctccagtc acccccaata aactcattct tcattgcatc    300
tatcgatcgg attctgtcca attgcctaat ggagttggct ccagtcgagc tgattggcaa    360
agctcttgcg ccatattagc gagcaaagtc gtttcccaag agcaacctac tgataaatct    420
agtgaagatt cacgtggtgc tgatcatgtt gctgctgtga acgggcacaa ggcctctatt    480
gatcttggtt tagtccctct taacaaaggt tctagtgatg gcgactccaa taacaaaaag    540
ccaacaaagt cgttaagtat caccgacctc tcaccggctc ctatgcacgg ctctcagctc    600
cgtgttgctt atcaaggggt tcccggcgca tattcggagg ctgcagcagg aaaagcttat    660
ccaaactgtg aagccatccc atgtgatcaa tttgacgtgg ttttccaggc ggtggagctt    720
tggatagcag atcgtgcagt tttaccagct gagaattctc taggtggatc aattcataga    780
aattatgatt tgctccttcg ccacaacctc cacatcgtcg gtgaagtaca atttccagtc    840
caccattgtc tcttagccct acccggtgtc cgtaaggagt atattactcg agtgatctct    900
caccctcaag cacttgcaca atgtgagcta acgctcactg aactcgggct gcatgctgtc    960
cgggaggcag tagatgacac ggctggcgct gcagagtaca tagcctctaa caatctccgc   1020
aacacggcag ccatagccag tgcacgcgcg gcagagctgt acggactgca aatactagcc   1080
gatggtatcc aggacgataa aagcaacgtt acgcgattct tgatgttggc tcgtgagcca   1140
ataatccctc gcacggaccg tccattcaag acaagcatcg tgttcgcaca cgataagggg   1200
acgagcgtgc ttttcaaggt gctatcagcg ttcgcattcc gtaacatcaa cttgacgaag   1260
atcgagtcac ggccacaccg agattgcccg atcaggctag tggacgatgc aagtgccggg   1320
acggcaaagc actttgagta catgttttac ttggattttg aagcgtcgat ggcagaagtt   1380
agggcacaga atgcattggc agaggtgcag gagttcactt ctttcttaag ggtgttgggg   1440
agctatccta tggacatgac tccttggtgc ccttcaagga gtgattgaca aaacccacca   1500
ataaaatatt acaaaaaaag cccttaaaag tgttattatt tgcacaagaa agggctatta   1560
ttttatttct tttgcaatct tttttatatt aattcaaagt aaatattaaa aatagttgtg   1620
gatgcaatgt ctaagaatgt gaataccatt tggtatactc aatcctttcc ttagtatgct   1680
atgccaaatt attaggggca ttaatgtgta tgcatatttt actaataaaa gtttcaggtt   1740
tttagaaaaa aaaaaaaaaa                                                1760
```

<210> SEQ ID NO 4
<211> LENGTH: 429
<212> TYPE: PRT
<213> ORGANISM: Hevea brasiliensis

<400> SEQUENCE: 4

```
Met Met Gln Ala Ile Ser Pro Pro Ser Pro Leu Lys Leu Leu Val Pro
1               5                   10                  15

Thr Arg Pro Arg Leu Ala Pro Val Thr Pro Asn Lys Leu Ile Leu His
            20                  25                  30

Cys Ile Tyr Arg Ser Asp Ser Val Gln Leu Pro Asn Gly Val Gly Ser
        35                  40                  45

Ser Arg Ala Asp Trp Gln Ser Ser Cys Ala Ile Leu Ala Ser Lys Val
    50                  55                  60

Val Ser Gln Glu Gln Pro Thr Asp Lys Ser Ser Glu Asp Ser Arg Gly
```

-continued

```
65                  70                  75                  80

Ala Asp His Val Ala Ala Val Asn Gly His Lys Ala Ser Ile Asp Leu
                85                  90                  95

Gly Leu Val Pro Leu Asn Lys Gly Ser Ser Asp Gly Asp Ser Asn Asn
            100                 105                 110

Lys Lys Pro Thr Lys Ser Leu Ser Ile Thr Asp Leu Ser Pro Ala Pro
        115                 120                 125

Met His Gly Ser Gln Leu Arg Val Ala Tyr Gln Gly Val Pro Gly Ala
    130                 135                 140

Tyr Ser Glu Ala Ala Ala Gly Lys Ala Tyr Pro Asn Cys Glu Ala Ile
145                 150                 155                 160

Pro Cys Asp Gln Phe Asp Val Val Phe Gln Ala Val Glu Leu Trp Ile
                165                 170                 175

Ala Asp Arg Ala Val Leu Pro Ala Glu Asn Ser Leu Gly Gly Ser Ile
            180                 185                 190

His Arg Asn Tyr Asp Leu Leu Leu Arg His Asn Leu His Ile Val Gly
        195                 200                 205

Glu Val Gln Phe Pro Val His His Cys Leu Leu Ala Leu Pro Gly Val
    210                 215                 220

Arg Lys Glu Tyr Ile Thr Arg Val Ile Ser His Pro Gln Ala Leu Ala
225                 230                 235                 240

Gln Cys Glu Leu Thr Leu Thr Glu Leu Gly Leu His Ala Val Arg Glu
                245                 250                 255

Ala Val Asp Asp Thr Ala Gly Ala Ala Glu Tyr Ile Ala Ser Asn Asn
            260                 265                 270

Leu Arg Asn Thr Ala Ala Ile Ala Ser Ala Arg Ala Ala Glu Leu Tyr
        275                 280                 285

Gly Leu Gln Ile Leu Ala Asp Gly Ile Gln Asp Asp Lys Ser Asn Val
    290                 295                 300

Thr Arg Phe Leu Met Leu Ala Arg Glu Pro Ile Ile Pro Arg Thr Asp
305                 310                 315                 320

Arg Pro Phe Lys Thr Ser Ile Val Phe Ala His Asp Lys Gly Thr Ser
                325                 330                 335

Val Leu Phe Lys Val Leu Ser Ala Phe Ala Phe Arg Asn Ile Asn Leu
            340                 345                 350

Thr Lys Ile Glu Ser Arg Pro His Arg Asp Cys Pro Ile Arg Leu Val
        355                 360                 365

Asp Asp Ala Ser Ala Gly Thr Ala Lys His Phe Glu Tyr Met Phe Tyr
    370                 375                 380

Leu Asp Phe Glu Ala Ser Met Ala Glu Val Arg Ala Gln Asn Ala Leu
385                 390                 395                 400

Ala Glu Val Gln Glu Phe Thr Ser Phe Leu Arg Val Leu Gly Ser Tyr
                405                 410                 415

Pro Met Asp Met Thr Pro Trp Cys Pro Ser Arg Ser Asp
            420                 425
```

<210> SEQ ID NO 5
<211> LENGTH: 1631
<212> TYPE: DNA
<213> ORGANISM: Hevea brasiliensis

<400> SEQUENCE: 5

```
tggttcattc attcattcac ttccaaagag agagaggaga aaaactatgg gcaaggaaaa      60

cgatagcgtt ccatcgtcgg cgccaggctt caagctccta ggattttcta acttcgtcag     120
```

-continued

```
aacaaatcct cgatccgatc ttttcaaggt caagcgcttt caccacgtgg agttctggtg    180

cactgatgct accaatacgg cttgtcgctt ctcctgggga cttggaatgc ctttcgtagc    240

taaatccgat ctttccactg gcaacgtcac ccatgcttcc tatctacttc gctccggcga    300

cctcagcttc ctttttaccg ctccctactc tcctactatt gcttccatgg agaacttttc    360

acacactgcc accgcatcta tcccaacctt cagtcatgaa gcgtgccgga atttctcagc    420

taagcacgga cttggtgttc gagccatcgc catagaagtt gaggacgcag aaatcgcgta    480

caacactagc gtcgcgcgcg gcgccttacc catgggcgga ccaataacgc tcgataatcg    540

tgccgttgtt gcggaagttc atttatatgg ggatgtagtt ttgcgatata ttagttacaa    600

gaactcaaac cctaacctta atgattctag tcccgatagt tggtttctgc caaaatttga    660

atcagtagat gaggcttcat cgtttccttt ggattacggg attcggcgat tggaccatgc    720

ggttggaaac gtgccggaat tagctccagc ggtctcttac gtcaaggagt tcaccggttt    780

ccatgagttt gcggagttca cggcggagga tgtggggact agtgagagcg gattgaactc    840

gttggttttg gcgaataatg aagacacagt tttgctgccg ctgaatgagc cggtgtttgg    900

caccaagagg aaaagccaaa tacaaacata cttggagcac aatgaaggag ctggtctgca    960

gcatttggcg cttgtgagtg aagatatatt caagacctta agggaaatgc ggcggaggag   1020

cggcgttgga ggatttgact ttatgccgtc tccgccgcca acatattatc ggaatttgaa   1080

gaacagggta ggggatgttt tgactgatga gcagatcaag gagtgtgagg agttgggaat   1140

tttggtggat agggatgatc aggggacctt gctccagatt ttcactaagc ctgttggcga   1200

taggccaacc atctttatag agataattca aagggtaggc tgcatgataa aggatgagac   1260

ggggaaagaa taccagaagg gtggatgcgg aggttttggg aagggaaact tttcagagct   1320

attcaagtct attgaggaat acgagaagac acttgaagcc aaacgaaatg cagaagcccg   1380

ctaaggcatg aatatgaact tggaatgcca tcaaccgtta ccatgtcact gaaatagtgt   1440

agccatgcta tttaaataac agtgaaactg aaaagataga ataagatgat aggaaacttt   1500

gtggttgttg gctgtgtaaa acttaataag attagaagct acttgtttgt tgcctgtgta   1560

aactcactaa ttgatgaaaa taatttagct aatgataata tattgttgaa ggtgcgaaaa   1620

aaaaaaaaaa a                                                        1631
```

```
<210> SEQ ID NO 6
<211> LENGTH: 445
<212> TYPE: PRT
<213> ORGANISM: Hevea brasiliensis

<400> SEQUENCE: 6

Met Gly Lys Glu Asn Asp Ser Val Pro Ser Ser Ala Pro Gly Phe Lys
1               5                   10                  15

Leu Leu Gly Phe Ser Asn Phe Val Arg Thr Asn Pro Arg Ser Asp Leu
            20                  25                  30

Phe Lys Val Lys Arg Phe His His Val Glu Phe Trp Cys Thr Asp Ala
        35                  40                  45

Thr Asn Thr Ala Cys Arg Phe Ser Trp Gly Leu Gly Met Pro Phe Val
    50                  55                  60

Ala Lys Ser Asp Leu Ser Thr Gly Asn Val Thr His Ala Ser Tyr Leu
65                  70                  75                  80

Leu Arg Ser Gly Asp Leu Ser Phe Leu Phe Thr Ala Pro Tyr Ser Pro
                85                  90                  95

Thr Ile Ala Ser Met Glu Asn Phe Ser His Thr Ala Thr Ala Ser Ile
            100                 105                 110
```

-continued

```
Pro Thr Phe Ser His Glu Ala Cys Arg Asn Phe Ser Ala Lys His Gly
        115                 120                 125

Leu Gly Val Arg Ala Ile Ala Ile Glu Val Glu Asp Ala Glu Ile Ala
    130                 135                 140

Tyr Asn Thr Ser Val Ala Arg Gly Ala Leu Pro Met Gly Gly Pro Ile
145                 150                 155                 160

Thr Leu Asp Asn Arg Ala Val Val Ala Glu Val His Leu Tyr Gly Asp
                165                 170                 175

Val Val Leu Arg Tyr Ile Ser Tyr Lys Asn Ser Asn Pro Asn Leu Asn
            180                 185                 190

Asp Ser Ser Pro Asp Ser Trp Phe Leu Pro Lys Phe Glu Ser Val Asp
        195                 200                 205

Glu Ala Ser Ser Phe Pro Leu Asp Tyr Gly Ile Arg Arg Leu Asp His
    210                 215                 220

Ala Val Gly Asn Val Pro Glu Leu Ala Pro Ala Val Ser Tyr Val Lys
225                 230                 235                 240

Glu Phe Thr Gly Phe His Glu Phe Ala Glu Phe Thr Ala Glu Asp Val
                245                 250                 255

Gly Thr Ser Glu Ser Gly Leu Asn Ser Leu Val Leu Ala Asn Asn Glu
            260                 265                 270

Asp Thr Val Leu Leu Pro Leu Asn Glu Pro Val Phe Gly Thr Lys Arg
        275                 280                 285

Lys Ser Gln Ile Gln Thr Tyr Leu Glu His Asn Glu Gly Ala Gly Leu
    290                 295                 300

Gln His Leu Ala Leu Val Ser Glu Asp Ile Phe Lys Thr Leu Arg Glu
305                 310                 315                 320

Met Arg Arg Arg Ser Gly Val Gly Gly Phe Asp Phe Met Pro Ser Pro
                325                 330                 335

Pro Pro Thr Tyr Tyr Arg Asn Leu Lys Asn Arg Val Gly Asp Val Leu
            340                 345                 350

Thr Asp Glu Gln Ile Lys Glu Cys Glu Glu Leu Gly Ile Leu Val Asp
        355                 360                 365

Arg Asp Asp Gln Gly Thr Leu Leu Gln Ile Phe Thr Lys Pro Val Gly
    370                 375                 380

Asp Arg Pro Thr Ile Phe Ile Glu Ile Ile Gln Arg Val Gly Cys Met
385                 390                 395                 400

Ile Lys Asp Glu Thr Gly Lys Glu Tyr Gln Lys Gly Gly Cys Gly Gly
                405                 410                 415

Phe Gly Lys Gly Asn Phe Ser Glu Leu Phe Lys Ser Ile Glu Glu Tyr
            420                 425                 430

Glu Lys Thr Leu Glu Ala Lys Arg Asn Ala Glu Ala Arg
        435                 440                 445


<210> SEQ ID NO 7
<211> LENGTH: 1793
<212> TYPE: DNA
<213> ORGANISM: Hevea brasiliensis

<400> SEQUENCE: 7

tgaagaccag aatgacttcc tccatcgcct tcaagtcctt caccggactc cgccattcct      60

cggctgaacc tcccaaactt cattcccagt tacacaacat ttcccctccc aactattgcc     120

agcgccacct tcagataacc gctggcatat ccagtcccaa gctccagaac cgcaacctca     180

gagtagcagt catcggcggt ggccccgccg gtggcgcagc cgccgagacc cttgctaaag     240
```

-continued

```
gtggcattga gacttacctc atcgaacgca agctcgacaa ctgcaaacca tgcggcggag    300

caattcctct ttgcatggtg ggcgagtttg acttgccatt agacatcata gaccgcaagg    360

tgaccaagat gaagatgatc tccccttcca acatcgccgt ggacattggg caaactctga    420

agccccacga gtacattggg atggtgagac gcgaggtgct tgattcttac ttgagagaga    480

gagcggcgag taatggggcc aatgtcatca atggtttgtt cttgaaaatg gaccttccaa    540

agggtggtaa aggcagcgag actgcacctt atgtcctcca ttacacggag tataatggaa    600

aggtaggtgg ggcaggacag aagaagactc tggaggttga tgcagtaatt ggtgctgatg    660

gagccaattc ccgtgttgcc aagtccattg gtgctggtga ttatgactac gccattgctt    720

ttcaggagag aatcagaatc cctgatgata aaatggtgta ctatgagaac ctagctgaaa    780

tgtatgtcgg tgatgatgta tctccagact tttatggatg ggtgttcccc aaatgtgacc    840

atgttgctgt tggaactggc acagtcactc acaaaggaga catcaagaag ttccaattag    900

ctacaagaaa tagagccaaa gacaagatcc ttgggggcaa gattattcga gtagaggcac    960

acccaatacc agaacacccg aggccacgca ggttatcaga cagagtagca ctagtagggg   1020

atgcggcagg gtatgtgacg aaatgttcag gcgagggcat ctactttgcg gcgaagagtg   1080

ggagaatgtg cgcggaggca atcgttgagg ggtcagggaa tgggaagagg atggtggatg   1140

agagtgacct gaggaagtac ttggagaaat gggacaaaac gtattggcca acatacaagg   1200

tgctggatgt gttgcagaaa gtattctaca gatcgaaccc agcaagagag gcattcgtgg   1260

agatgtgtgc agatgagtat gtgcagaaaa tgactttcga tagctatttg tacaagaagg   1320

tggtacccgg gaatcctttg gacgatttga agttggcttt caataccatt gggagcttgg   1380

tgagggctaa tgctcttaga aaggagatga acaagcttag cgtatgagct acctatgcta   1440

agatttatgt gtctttgttc atttatgtat taattaaatc ttagctagca tatatgctaa   1500

gatttaaaaa tttagctacg atatttatgt gtcttttgtt cttgctgtta aaaatatgat   1560

agctaaagag gaaatgggat gttcagattg ttcatgtcta cagagaagca agtgttgttg   1620

cagactggct tgccaacagt gctttttctt ttgatcttgg ccctcacata ctggtttctc   1680

cagctgggtc gactgctttt tcaagatgcc tctggttttg ctcagtgcag agacgtgctg   1740

atgcttcctt ggtttgagtt tgtcttgttc ctttaaccaa aaaaaaaaaa aaa          1793
```

```
<210> SEQ ID NO 8
<211> LENGTH: 471
<212> TYPE: PRT
<213> ORGANISM: Hevea brasiliensis

<400> SEQUENCE: 8

Met Thr Ser Ser Ile Ala Phe Lys Ser Phe Thr Gly Leu Arg His Ser
1               5                   10                  15

Ser Ala Glu Pro Pro Lys Leu His Ser Gln Leu His Asn Ile Ser Pro
            20                  25                  30

Pro Asn Tyr Cys Gln Arg His Leu Gln Ile Thr Ala Gly Ile Ser Ser
        35                  40                  45

Pro Lys Leu Gln Asn Arg Asn Leu Arg Val Ala Val Ile Gly Gly Gly
    50                  55                  60

Pro Ala Gly Gly Ala Ala Ala Glu Thr Leu Ala Lys Gly Gly Ile Glu
65                  70                  75                  80

Thr Tyr Leu Ile Glu Arg Lys Leu Asp Asn Cys Lys Pro Cys Gly Gly
                85                  90                  95

Ala Ile Pro Leu Cys Met Val Gly Glu Phe Asp Leu Pro Leu Asp Ile
            100                 105                 110
```

```
Ile Asp Arg Lys Val Thr Lys Met Lys Met Ile Ser Pro Ser Asn Ile
        115                 120                 125

Ala Val Asp Ile Gly Gln Thr Leu Lys Pro His Glu Tyr Ile Gly Met
    130                 135                 140

Val Arg Arg Glu Val Leu Asp Ser Tyr Leu Arg Glu Arg Ala Ala Ser
145                 150                 155                 160

Asn Gly Ala Asn Val Ile Asn Gly Leu Phe Leu Lys Met Asp Leu Pro
                165                 170                 175

Lys Gly Gly Lys Gly Ser Glu Thr Ala Pro Tyr Val Leu His Tyr Thr
            180                 185                 190

Glu Tyr Asn Gly Lys Val Gly Gly Ala Gly Gln Lys Lys Thr Leu Glu
        195                 200                 205

Val Asp Ala Val Ile Gly Ala Asp Gly Ala Asn Ser Arg Val Ala Lys
    210                 215                 220

Ser Ile Gly Ala Gly Asp Tyr Asp Tyr Ala Ile Ala Phe Gln Glu Arg
225                 230                 235                 240

Ile Arg Ile Pro Asp Asp Lys Met Val Tyr Tyr Glu Asn Leu Ala Glu
                245                 250                 255

Met Tyr Val Gly Asp Asp Val Ser Pro Asp Phe Tyr Gly Trp Val Phe
            260                 265                 270

Pro Lys Cys Asp His Val Ala Val Gly Thr Gly Thr Val Thr His Lys
        275                 280                 285

Gly Asp Ile Lys Lys Phe Gln Leu Ala Thr Arg Asn Arg Ala Lys Asp
    290                 295                 300

Lys Ile Leu Gly Gly Lys Ile Ile Arg Val Glu Ala His Pro Ile Pro
305                 310                 315                 320

Glu His Pro Arg Pro Arg Arg Leu Ser Asp Arg Val Ala Leu Val Gly
                325                 330                 335

Asp Ala Ala Gly Tyr Val Thr Lys Cys Ser Gly Glu Gly Ile Tyr Phe
            340                 345                 350

Ala Ala Lys Ser Gly Arg Met Cys Ala Glu Ala Ile Val Glu Gly Ser
        355                 360                 365

Gly Asn Gly Lys Arg Met Val Asp Glu Ser Asp Leu Arg Lys Tyr Leu
    370                 375                 380

Glu Lys Trp Asp Lys Thr Tyr Trp Pro Thr Tyr Lys Val Leu Asp Val
385                 390                 395                 400

Leu Gln Lys Val Phe Tyr Arg Ser Asn Pro Ala Arg Glu Ala Phe Val
                405                 410                 415

Glu Met Cys Ala Asp Glu Tyr Val Gln Lys Met Thr Phe Asp Ser Tyr
            420                 425                 430

Leu Tyr Lys Lys Val Val Pro Gly Asn Pro Leu Asp Asp Leu Lys Leu
        435                 440                 445

Ala Phe Asn Thr Ile Gly Ser Leu Val Arg Ala Asn Ala Leu Arg Lys
    450                 455                 460

Glu Met Asn Lys Leu Ser Val
465                 470


<210> SEQ ID NO 9
<211> LENGTH: 1563
<212> TYPE: DNA
<213> ORGANISM: Hevea brasiliensis

<400> SEQUENCE: 9

gaacacagaa agagagatta gtagtagcag tagttttgga cttctgatta acttaagaag      60
```

-continued

```
catcagttcc taatcagttg gagatggtgg ttatggagtc tctgcttctt gggtcgtttc     120

ctaagccttc ttcggtcact tctggtggaa attgttggga gagtaaaaat ttcagagtgg     180

gtcactctcc aagggtaacc cgttctatag catcagtcag agttgccagg tgcagaacat     240

ggaacgtcct agaaagatat tatgttgcaa agtttccgct tcctcgaatg aaccatcatc     300

ttagatgtag tgtggaaaga tctaacattt atcagagaaa aaagggtgcc catttcttgg     360

tgtataccgc ctctggacag cctcttgaat ctgagtcaga tgcttatagt cctaagatta     420

cttcaaattc tgttctcaat gcattagatg ctttctacag attttcacgt cctcatacgg     480

ttataggcac agctttgagc atcttatcgg tttctctcct tgcagtagag aaactctcgg     540

atctttctcc actgttcttg acaggtgttt tggaggcagt ggttgctgcc ctcatgatga     600

atgtatacat agttggttta aatcaattaa ctgacatcga aatagaccaa gttaacaagc     660

catatcttcc attggcatct ggagagtatt ccaagggcat tggtgttctg aatgtggcat     720

ctttctccat aatgagcttt tggcttggat gggttgttgg ttcatggcca ttgttttggg     780

ctctttttgt cagttttgtt cttggaacag catattcaat caatttgcca ttattgagat     840

ggaaaaggtt tgcatttgtt gcagcaatgt gcatcttagt tgtccgggca gtgatcgttc     900

aacttgcctt ttatctgcac atgcagaccc acgtgtacag aagacctact gtcttttcca     960

ggcctctgat tttgcaact gcattcatgt gcttattctc tgttgttata gcattattca     1020

aggatatacc tgatattgaa ggggataaga tatttggtat ccgatccttt acagtgcgct    1080

tgggccaaga acgggttttc tggacctgta tttctctgct tgaaatagct tatggtgttg    1140

ctattttagt tggagcagct tcttcccaca cctggagcaa gtgtatcacg gttctggggc    1200

atgccatatt ggcttcaata ctgtggaacc gtgctaaagc tgttgatctc aagagcaaag    1260

ctgctataac ttcatgttac atgtttattt ggaagctctt ttatgcagaa tacttgctca    1320

taccactcgt aagatgagca tgcaaagcat tgtggagaga aggaaactgc agccgtctct    1380

aaaaatggag tattctactg aaacattaat gcctagaaag aggatactat ggtttgcttg    1440

caagttctgt atgcctatca tttatctcga acaattgtaa tgctgggaga aaaaaatgca    1500

attactatgt aatggcattg tattagtaca caatttatta tttgcattta aaaaaaaaaa    1560

aaa                                                                  1563


<210> SEQ ID NO 10
<211> LENGTH: 414
<212> TYPE: PRT
<213> ORGANISM: Hevea brasiliensis

<400> SEQUENCE: 10

Met Glu Ser Leu Leu Leu Gly Ser Phe Pro Lys Pro Ser Ser Val Thr
1               5                   10                  15

Ser Gly Gly Asn Cys Trp Glu Ser Lys Asn Phe Arg Val Gly His Ser
            20                  25                  30

Pro Arg Val Thr Arg Ser Ile Ala Ser Val Arg Val Ala Arg Cys Arg
        35                  40                  45

Thr Trp Asn Val Leu Glu Arg Tyr Tyr Val Ala Lys Phe Pro Leu Pro
    50                  55                  60

Arg Met Asn His His Leu Arg Cys Ser Val Glu Arg Ser Asn Ile Tyr
65                  70                  75                  80

Gln Arg Lys Lys Gly Ala His Phe Leu Val Tyr Thr Ala Ser Gly Gln
                85                  90                  95

Pro Leu Glu Ser Glu Ser Asp Ala Tyr Ser Pro Lys Ile Thr Ser Asn
            100                 105                 110
```

```
Ser Val Leu Asn Ala Leu Asp Ala Phe Tyr Arg Phe Ser Arg Pro His
        115                 120                 125

Thr Val Ile Gly Thr Ala Leu Ser Ile Leu Ser Val Ser Leu Leu Ala
    130                 135                 140

Val Glu Lys Leu Ser Asp Leu Ser Pro Leu Phe Leu Thr Gly Val Leu
145                 150                 155                 160

Glu Ala Val Val Ala Ala Leu Met Met Asn Val Tyr Ile Val Gly Leu
                165                 170                 175

Asn Gln Leu Thr Asp Ile Glu Ile Asp Gln Val Asn Lys Pro Tyr Leu
            180                 185                 190

Pro Leu Ala Ser Gly Glu Tyr Ser Lys Gly Ile Gly Val Leu Asn Val
        195                 200                 205

Ala Ser Phe Ser Ile Met Ser Phe Trp Leu Gly Trp Val Val Gly Ser
    210                 215                 220

Trp Pro Leu Phe Trp Ala Leu Phe Val Ser Phe Val Leu Gly Thr Ala
225                 230                 235                 240

Tyr Ser Ile Asn Leu Pro Leu Leu Arg Trp Lys Arg Phe Ala Phe Val
                245                 250                 255

Ala Ala Met Cys Ile Leu Val Val Arg Ala Val Ile Val Gln Leu Ala
            260                 265                 270

Phe Tyr Leu His Met Gln Thr His Val Tyr Arg Arg Pro Thr Val Phe
        275                 280                 285

Ser Arg Pro Leu Ile Phe Ala Thr Ala Phe Met Cys Leu Phe Ser Val
    290                 295                 300

Val Ile Ala Leu Phe Lys Asp Ile Pro Asp Ile Glu Gly Asp Lys Ile
305                 310                 315                 320

Phe Gly Ile Arg Ser Phe Thr Val Arg Leu Gly Gln Glu Arg Val Phe
                325                 330                 335

Trp Thr Cys Ile Ser Leu Leu Glu Ile Ala Tyr Gly Val Ala Ile Leu
            340                 345                 350

Val Gly Ala Ala Ser Ser His Thr Trp Ser Lys Cys Ile Thr Val Leu
        355                 360                 365

Gly His Ala Ile Leu Ala Ser Ile Leu Trp Asn Arg Ala Lys Ala Val
    370                 375                 380

Asp Leu Lys Ser Lys Ala Ala Ile Thr Ser Cys Tyr Met Phe Ile Trp
385                 390                 395                 400

Lys Leu Phe Tyr Ala Glu Tyr Leu Leu Ile Pro Leu Val Arg
                405                 410
```

<210> SEQ ID NO 11
<211> LENGTH: 1410
<212> TYPE: DNA
<213> ORGANISM: Hevea brasiliensis

<400> SEQUENCE: 11

```
gatttgaccg gcactttgct attctagccg ccacatcatg cttactgaat aatcacaaac     60

caccgccact gccgattaat aagctggtgt ctgcaagtgg gtttcctttg aaatcttcaa    120

attcacttgt tctccttggt gggtaatctt tggttcatcc attcatggct tcctcaatgc    180

ttagtggagc tgagaacctc actctcatga aaggcataag cccaaaagtg aaagggttag    240

gtttttcgcg gtcagatttt cacgggaacc actttcccgg agtgacaatt acttgctcta    300

gaatcttcag gacaagaaca atgatgccca agtgcagttt atcagcctct aggccagctt    360

ctcagcccaa gttcatccaa cacaagaaag aggctttttg gttctacaga ttcctctcag    420
```

-continued

```
ttgtatatga ccatattata aatcctggtc actggactga ggacatgaga gatgatgcac    480

tagagcctgc tgatctcagt gacaggaata tggtagttgt agatgtgggc ggtggtactg    540

gtttcactac tttgggtata gtgaagcatg tggatgccaa aatgtcacc attcttgatc     600

agtccccgca tcagcttgca aaggccaagc agaaggagcc cttgaaggag tgtaagatta    660

ttgagggcga cgcagaggat ctgccatttc ctaccgatta tgctgacaga tatgtgtccg    720

ctgggagtat tgagtattgg ccagatccac aacgtggcat caaggaagca tacagggtcc    780

tgaaacacgg aggaaaagcc tgcttaattg gtccagtgca tccaacattt tggttgtctc    840

gtttctttgc agatgtttgg atgcttttcc caaaggagga agagtacatt gaatggtttg    900

aaaaggctgg gtttaaggat gtccaactga agcgtatagg cccaaaatgg tatcgtggtg    960

ttcgccggca tgggctgatc atgggatgtt ctgtgacagg tgttaaacct gcatatggag   1020

attctccttt acagcttggt ccaaagcaag aggacgtggc aaagccggtg aacccatttg   1080

tgttccttct gcgttttatt ttgggtgcca tggcagcaac atactatgta ctggtgccta   1140

tctacatgtg gctcaaagat caaattgtac ccgaaggtag accaatctaa gagggattat   1200

ggagttgctt ttgtgggctg cttcttcttc ttcttcttat ttattttttt tttatttttt   1260

taaagtttcc acctgtgtgg tcattagaac gagtatgcaa gactaggtga gatgagtgta   1320

tcattgaaca cttctaagac tttttctaaa gtttcttttg aaataataat agaagctgaa   1380

agtcgtcatt ggaacgaaaa aaaaaaaaaa                                    1410
```

<210> SEQ ID NO 12
<211> LENGTH: 341
<212> TYPE: PRT
<213> ORGANISM: Hevea brasiliensis

<400> SEQUENCE: 12

```
Met Ala Ser Ser Met Leu Ser Gly Ala Glu Asn Leu Thr Leu Met Lys
1               5                   10                  15

Gly Ile Ser Pro Lys Val Lys Gly Leu Gly Phe Ser Arg Ser Asp Phe
            20                  25                  30

His Gly Asn His Phe Pro Gly Val Thr Ile Thr Cys Ser Arg Ile Phe
        35                  40                  45

Arg Thr Arg Thr Met Met Pro Lys Cys Ser Leu Ser Ala Ser Arg Pro
    50                  55                  60

Ala Ser Gln Pro Lys Phe Ile Gln His Lys Lys Glu Ala Phe Trp Phe
65                  70                  75                  80

Tyr Arg Phe Leu Ser Val Val Tyr Asp His Ile Ile Asn Pro Gly His
                85                  90                  95

Trp Thr Glu Asp Met Arg Asp Asp Ala Leu Glu Pro Ala Asp Leu Ser
            100                 105                 110

Asp Arg Asn Met Val Val Val Asp Val Gly Gly Gly Thr Gly Phe Thr
        115                 120                 125

Thr Leu Gly Ile Val Lys His Val Asp Ala Lys Asn Val Thr Ile Leu
    130                 135                 140

Asp Gln Ser Pro His Gln Leu Ala Lys Ala Lys Gln Lys Glu Pro Leu
145                 150                 155                 160

Lys Glu Cys Lys Ile Ile Glu Gly Asp Ala Glu Asp Leu Pro Phe Pro
                165                 170                 175

Thr Asp Tyr Ala Asp Arg Tyr Val Ser Ala Gly Ser Ile Glu Tyr Trp
            180                 185                 190

Pro Asp Pro Gln Arg Gly Ile Lys Glu Ala Tyr Arg Val Leu Lys His
        195                 200                 205
```

```
Gly Gly Lys Ala Cys Leu Ile Gly Pro Val His Pro Thr Phe Trp Leu
    210                 215                 220

Ser Arg Phe Phe Ala Asp Val Trp Met Leu Phe Pro Lys Glu Glu Glu
225                 230                 235                 240

Tyr Ile Glu Trp Phe Glu Lys Ala Gly Phe Lys Asp Val Gln Leu Lys
                245                 250                 255

Arg Ile Gly Pro Lys Trp Tyr Arg Gly Val Arg Arg His Gly Leu Ile
            260                 265                 270

Met Gly Cys Ser Val Thr Gly Val Lys Pro Ala Tyr Gly Asp Ser Pro
        275                 280                 285

Leu Gln Leu Gly Pro Lys Gln Glu Asp Val Ala Lys Pro Val Asn Pro
    290                 295                 300

Phe Val Phe Leu Leu Arg Phe Ile Leu Gly Ala Met Ala Ala Thr Tyr
305                 310                 315                 320

Tyr Val Leu Val Pro Ile Tyr Met Trp Leu Lys Asp Gln Ile Val Pro
                325                 330                 335

Glu Gly Arg Pro Ile
            340


<210> SEQ ID NO 13
<211> LENGTH: 1837
<212> TYPE: DNA
<213> ORGANISM: Hevea brasiliensis

<400> SEQUENCE: 13

ttataaagat tctgataaaa caattctgta aattgcagat cgctagagac tcagagagag     60

agagagagag agaggtacac tatgcttcat tactatccaa gcccatgcct caacacccct    120

ccaaagtatc aagtccttga tccaggtcaa gttacaacag taacagtgtt aaagaaacaa    180

gtaaatcaca tcctgaaaga aagccagtgc aagaagccca taatttgttc cttaagatcg    240

ttatcttggg ccaaaaatag caggaaaaaa gagttatatg tgttgagaaa tctacgtata    300

ctaactagaa agaatggtat tcctgccatt tttttacaga ataattggct tgcaccaaat    360

tctgaggatg gtgatgatat ttgttcaagt tctaagaggg gaccaattct agagcactta    420

aattccttat atcagttttc acgtcctcac actgtgattg gcactattat aggaataaca    480

tcagtttccc ttcttccggt agaaacaatt gttgacctgt ctcccacata ttttattggg    540

ctactgaaag cactggtgcc ttcagtgttg atgaacattt acgtggtggg attgaatcaa    600

ttgtttgatg ttgaaattga caaggtaaat aaaccctatc tcccacttgc ttctggcaag    660

ttctcaatgg caactggtat cctaattgtt tctgcatctt tattgctgag tctttatatg    720

ggaattacgt ttcaatctcc accacttctt gcagccctcc ttataagttt tgcccttgga    780

agtgtatatt ccattgaact tccctttctg agatggaaga aacatgcttt tcttgctgca    840

agttgtattc tgatcgtaag agcaatggtt gttcaacttg ccttctttgt acacatccag    900

aaatttgttc ttggaaaatc catatttatt cccagatcgt tgatgtttgc aactgctttc    960

atgtgcttct tctctgctgc tattgcacta ttcaaggaca tcccagatgt ggagggggac   1020

agagattatg ggatccaatc cttcagtgtc agccttggcc aagaaagagt cctttggctt   1080

tgcgttaaca tgctattagt ggcctatggt gctgctgtcg tacacggagc ttcttctcct   1140

tcttcgctcc taccagtcaa gcttatcaca atgatagggc atagcacaat tgcttggatt   1200

ttgtggatga aagcacaatt cgttgatctc accagccaga agtctattac ttctttttac   1260

atgttcatat ggaagttatt ctatgcggag tatttcctta tcccttttgt gcgttgagag   1320
```

-continued

```
tgacaaatat taaaggcttg caacttcaag aagacaataa cgtcccccag gaaccactgt   1380

tataacacag atgaaagaga ttgaggcatt gctggctggt ttcggttttt tttttttttt   1440

tttttttttt aataagcaat aagttaattt tattaataaa aagtagggca agaaaaattt   1500

agcatgagac acttagctaa accccgacct ggccaacaag cctctcctta gaacccaaat   1560

taagaggagc atgccaagcg aagacattgt tgggttatca ctcatgggat tagcaaaaat   1620

atatttatgc aaaggtggtt ttaccaagag gaacactgca ggtgatggtg gaggacaaga   1680

caaacactcc acttctatag aaaatattaa tggaaacacc tgcctaagaa aattttacca   1740

attcaattgg tgagtgcaaa gaaccttaag tgctttgtat ttttggctaa taaatgattg   1800

ctacatatac tattagtatc agaaaaaaaa aaaaaaa                            1837
```

```
<210> SEQ ID NO 14
<211> LENGTH: 411
<212> TYPE: PRT
<213> ORGANISM: Hevea brasiliensis

<400> SEQUENCE: 14

Met Leu His Tyr Tyr Pro Ser Pro Cys Leu Asn Thr Pro Pro Lys Tyr
1               5                   10                  15

Gln Val Leu Asp Pro Gly Gln Val Thr Thr Val Thr Val Leu Lys Lys
            20                  25                  30

Gln Val Asn His Ile Leu Lys Glu Ser Gln Cys Lys Lys Pro Ile Ile
        35                  40                  45

Cys Ser Leu Arg Ser Leu Ser Trp Ala Lys Asn Ser Arg Lys Lys Glu
    50                  55                  60

Leu Tyr Val Leu Arg Asn Leu Arg Ile Leu Thr Arg Lys Asn Gly Ile
65                  70                  75                  80

Pro Ala Ile Phe Leu Gln Asn Asn Trp Leu Ala Pro Asn Ser Glu Asp
                85                  90                  95

Gly Asp Asp Ile Cys Ser Ser Ser Lys Arg Gly Pro Ile Leu Glu His
            100                 105                 110

Leu Asn Ser Leu Tyr Gln Phe Ser Arg Pro His Thr Val Ile Gly Thr
        115                 120                 125

Ile Ile Gly Ile Thr Ser Val Ser Leu Leu Pro Val Glu Thr Ile Val
    130                 135                 140

Asp Leu Ser Pro Thr Tyr Phe Ile Gly Leu Leu Lys Ala Leu Val Pro
145                 150                 155                 160

Ser Val Leu Met Asn Ile Tyr Val Val Gly Leu Asn Gln Leu Phe Asp
                165                 170                 175

Val Glu Ile Asp Lys Val Asn Lys Pro Tyr Leu Pro Leu Ala Ser Gly
            180                 185                 190

Lys Phe Ser Met Ala Thr Gly Ile Leu Ile Val Ser Ala Ser Leu Leu
        195                 200                 205

Leu Ser Leu Tyr Met Gly Ile Thr Phe Gln Ser Pro Pro Leu Leu Ala
    210                 215                 220

Ala Leu Leu Ile Ser Phe Ala Leu Gly Ser Val Tyr Ser Ile Glu Leu
225                 230                 235                 240

Pro Phe Leu Arg Trp Lys Lys His Ala Phe Leu Ala Ala Ser Cys Ile
                245                 250                 255

Leu Ile Val Arg Ala Met Val Val Gln Leu Ala Phe Phe Val His Ile
            260                 265                 270

Gln Lys Phe Val Leu Gly Lys Ser Ile Phe Ile Pro Arg Ser Leu Met
        275                 280                 285
```

```
Phe Ala Thr Ala Phe Met Cys Phe Phe Ser Ala Ala Ile Ala Leu Phe
    290                 295                 300

Lys Asp Ile Pro Asp Val Glu Gly Asp Arg Asp Tyr Gly Ile Gln Ser
305                 310                 315                 320

Phe Ser Val Ser Leu Gly Gln Glu Arg Val Leu Trp Leu Cys Val Asn
                325                 330                 335

Met Leu Leu Val Ala Tyr Gly Ala Ala Val Val His Gly Ala Ser Ser
            340                 345                 350

Pro Ser Ser Leu Leu Pro Val Lys Leu Ile Thr Met Ile Gly His Ser
        355                 360                 365

Thr Ile Ala Trp Ile Leu Trp Met Lys Ala Gln Phe Val Asp Leu Thr
    370                 375                 380

Ser Gln Lys Ser Ile Thr Ser Phe Tyr Met Phe Ile Trp Lys Leu Phe
385                 390                 395                 400

Tyr Ala Glu Tyr Phe Leu Ile Pro Phe Val Arg
                405                 410


<210> SEQ ID NO 15
<211> LENGTH: 1282
<212> TYPE: DNA
<213> ORGANISM: Hevea brasiliensis

<400> SEQUENCE: 15

gagtggagtc tgcaactggg ttttctttac aacctccaga ttgacttgtt ttccttggtg     60

ggtaatcttt gattcatcta gtcatggcct ccttaatgct caatggagct gagaacttca    120

ctctcatgag cggcataacc ccaaaagggt taggtttttt gggttcggat tttcatggga    180

accactttcc tagagtgaat ttaatcagta gctctagaat ctccaggaca agaacagtga    240

tgcccaagtg caatttatca gcctctaggc cagcttctca gcccaggttc atccaacaca    300

agaaagaggc tttttggttc taccggttcc tgtcaattgt atatgatcat gtgataaatc    360

ctgggcactg gactgaggac atgagagacg atgcgctaga gcctgcggat ctcaataaca    420

ggaatttgct agttgtagat gttggcggtg gcaccggttt cactactttg ggtattgtaa    480

agcatgtgga tgcccaaaat gttaccattc ttgatcagtc cccgcatcag cttgcaaagg    540

ccaagcagaa ggagccctta aaggattgta agataattga gggcgacgca gaggatctgc    600

catttcctac tgattatgcg gacagatatg tgtccgctgg gagtattgag tactggccag    660

acccacaacg tggcatcaag gaagcataca gggtcctgaa actaggagga aaagcctgct    720

taattggtcc agtatatcca acattttggt tgtctcgctt ctttgcagat gtatggatgc    780

tcttcccaaa ggaagaagag tacattgaat ggtttgaaaa ggctgggttt aaggatgttc    840

aactgaagcg tattggccca aaatggtatc gtggtgttcg ccggcatggg ctaatcatgg    900

gatgttctgt gacaggggtt aaacctgcat ctggagattc tcctttaaag cttggtccaa    960

aggaagagga catagcaaag ccagtgaacc catttgtgtt ccttctgcgt tttattttgg   1020

gtggcttggc ggcagcgtac tatgtgctgg tgcctatcta catgtggctt aaagatcaaa   1080

ttgtacccaa gggtagacca atctgagact aaaagggatt tttagagttc cttaagtggg   1140

ccattttatt tttaatttat agacaatttc ctcctgtgtg ggcacacaag taaattagac   1200

atatgctttt aattagatgc ctctcctttg atttttctaa ttctagttgt gaaattcatt   1260

tttcaaaaca aaaaaaaaaa aa                                            1282


<210> SEQ ID NO 16
<211> LENGTH: 340
<212> TYPE: PRT
```

<213> ORGANISM: Hevea brasiliensis

<400> SEQUENCE: 16

```
Met Ala Ser Leu Met Leu Asn Gly Ala Glu Asn Phe Thr Leu Met Ser
1               5                   10                  15

Gly Ile Thr Pro Lys Gly Leu Gly Phe Leu Gly Ser Asp Phe His Gly
            20                  25                  30

Asn His Phe Pro Arg Val Asn Leu Ile Ser Ser Ser Arg Ile Ser Arg
        35                  40                  45

Thr Arg Thr Val Met Pro Lys Cys Asn Leu Ser Ala Ser Arg Pro Ala
    50                  55                  60

Ser Gln Pro Arg Phe Ile Gln His Lys Lys Glu Ala Phe Trp Phe Tyr
65                  70                  75                  80

Arg Phe Leu Ser Ile Val Tyr Asp His Val Ile Asn Pro Gly His Trp
                85                  90                  95

Thr Glu Asp Met Arg Asp Asp Ala Leu Glu Pro Ala Asp Leu Asn Asn
            100                 105                 110

Arg Asn Leu Leu Val Val Asp Val Gly Gly Gly Thr Gly Phe Thr Thr
        115                 120                 125

Leu Gly Ile Val Lys His Val Asp Ala Gln Asn Val Thr Ile Leu Asp
    130                 135                 140

Gln Ser Pro His Gln Leu Ala Lys Ala Lys Gln Lys Glu Pro Leu Lys
145                 150                 155                 160

Asp Cys Lys Ile Ile Glu Gly Asp Ala Glu Asp Leu Pro Phe Pro Thr
                165                 170                 175

Asp Tyr Ala Asp Arg Tyr Val Ser Ala Gly Ser Ile Glu Tyr Trp Pro
            180                 185                 190

Asp Pro Gln Arg Gly Ile Lys Glu Ala Tyr Arg Val Leu Lys Leu Gly
        195                 200                 205

Gly Lys Ala Cys Leu Ile Gly Pro Val Tyr Pro Thr Phe Trp Leu Ser
    210                 215                 220

Arg Phe Phe Ala Asp Val Trp Met Leu Phe Pro Lys Glu Glu Glu Tyr
225                 230                 235                 240

Ile Glu Trp Phe Glu Lys Ala Gly Phe Lys Asp Val Gln Leu Lys Arg
                245                 250                 255

Ile Gly Pro Lys Trp Tyr Arg Gly Val Arg Arg His Gly Leu Ile Met
            260                 265                 270

Gly Cys Ser Val Thr Gly Val Lys Pro Ala Ser Gly Asp Ser Pro Leu
        275                 280                 285

Lys Leu Gly Pro Lys Glu Glu Asp Ile Ala Lys Pro Val Asn Pro Phe
    290                 295                 300

Val Phe Leu Leu Arg Phe Ile Leu Gly Gly Leu Ala Ala Ala Tyr Tyr
305                 310                 315                 320

Val Leu Val Pro Ile Tyr Met Trp Leu Lys Asp Gln Ile Val Pro Lys
                325                 330                 335

Gly Arg Pro Ile
            340
```

<210> SEQ ID NO 17
<211> LENGTH: 2008
<212> TYPE: DNA
<213> ORGANISM: Hevea brasiliensis

<400> SEQUENCE: 17

```
tcatataaaa tattttttct aaggatcgct taaaacattt tccatgaaat tttcggtttt      60
```

-continued

```
cttctaaaag ttttatagaa tttaagcgca gttatctact gttaattttc tgtaatccaa    120

caatggaagc taacttccaa tgctcgctct accatcttca ccatttctct tccaatatgg    180

gatttcctgc tctaaaccct tgttccaccc ttaaaccttt ccgtttgaat caaagctccg    240

tcggaattca ttggcggtca ctgcaagtag ggtttcgatc atcgaggtcc cgactcttgg    300

tttccaattc ggtgactgac cgtcaaactt cgactgttga aagaggaggt actgagggtg    360

tggcctctgc aagtcccgtt tatgtcgcca ctcctcccaa ccgtgagctt cgaactcctc    420

acagcgggta ccattttgat ggaaccacgc ggcaattttt tgagggttgg tacttcaagg    480

tctctattcc tgagcggaag gagagctttt gtttcatgta ttctgtggag aatccagcat    540

ttcggaagaa attgtcgccc ttggaagtgg cacagcatgg acccagatcc actggagttg    600

gtgctcaaat tctcggggct tctgacaagt atatatgtca atattctgaa gaatctcaga    660

acttctgggg aagtaggcat gaactgatgt tggggaatac ttttgtggcc gagaaaggca    720

tgcagcctcc atccaaggag gttcctcctc aggagtttaa tagaatggtt tcagaaggtt    780

ttcaagtcac cccattatgg aatcaaggtt ttattcgtga tgatggcagg tcagattatg    840

tgaaaactgt gaaaactgca cgttgggagt acagtactcg ccctgtttat ggatggggta    900

atgtgggatc caaacaacag tccactgcag gctggcttgc tgcatttcct gtatttgaac    960

cccattggca aatatgcatg gcagccggac tttcaacagg ctggatagag tgggatggtg   1020

aaagatttga gttcaaagat gcaccttctt actcagaaaa gaactggggt ggaggctttc   1080

caaggaaatg gttttgggct cagtgtaata cctttgaagg tgcaagcgga gaagttgctt   1140

tgactgtggg tggtgggctg aggcaattgc ctggactaac tgagaccttt gaaaatgctg   1200

cgttgattgg agtgcattat gatggaattt tctatgaatt tgtaccatgg aaaggtgttg   1260

taacttggga aatcagccca tggggttact ggttcgtaac tgcagagaat gagacacatt   1320

tggttgaatt ggaggcaaca acaaaggatc cgggaacaac acttcgtgct ccaacaacag   1380

aggctggcct tgctccagct tgcaaagata cttgttatgg tgttctgaaa ttgaaattat   1440

gggaacgaag atatgatggc tctaagggca agataatttt ggatgttaca agtgacatgg   1500

cagcagtaga agttggtgga ggaccgtggt ttaacacctg gaaagggaag acaactacgc   1560

cagagcttct cagccgtgct ctgagagtgc ccttagacgt ggatgggatc ttcaattttc   1620

ttccactatt caaaccccct ggcttatagg cagttggttc aggtctttca ttgcaccaaa   1680

tcgatatctt tgcaactgga gaagtaagat ctggccagtg tggcatgaca tggtccgtct   1740

atatttccgt aggtggaatc ttatgaacat ttcatggcag caccaacctg tacttgatcg   1800

ccttttttcca tgtctgttca tcacttttat cactcagaca attctcgata gctccataga   1860

catttgatac attcttgcaa attttatgag gagtcggtat atgatatgct ttgaaatgat   1920

attgaaaatt tactttatgc ctgagagccg gtaaaaggag ctcaaatact aggatgcaag   1980

tgctcaaatt cagacaaaaa aaaaaaaa                                      2008
```

<210> SEQ ID NO 18
<211> LENGTH: 508
<212> TYPE: PRT
<213> ORGANISM: Hevea brasiliensis

<400> SEQUENCE: 18

```
Met Glu Ala Asn Phe Gln Cys Ser Leu Tyr His Leu His His Phe Ser
1               5                   10                  15

Ser Asn Met Gly Phe Pro Ala Leu Asn Pro Cys Ser Thr Leu Lys Pro
            20                  25                  30
```

-continued

```
Phe Arg Leu Asn Gln Ser Ser Val Gly Ile His Trp Arg Ser Leu Gln
        35                  40                  45

Val Gly Phe Arg Ser Ser Arg Ser Arg Leu Leu Val Ser Asn Ser Val
    50                  55                  60

Thr Asp Arg Gln Thr Ser Thr Val Glu Arg Gly Gly Thr Glu Gly Val
65                  70                  75                  80

Ala Ser Ala Ser Pro Val Tyr Val Ala Thr Pro Pro Asn Arg Glu Leu
                85                  90                  95

Arg Thr Pro His Ser Gly Tyr His Phe Asp Gly Thr Thr Arg Gln Phe
            100                 105                 110

Phe Glu Gly Trp Tyr Phe Lys Val Ser Ile Pro Glu Arg Lys Glu Ser
        115                 120                 125

Phe Cys Phe Met Tyr Ser Val Glu Asn Pro Ala Phe Arg Lys Lys Leu
    130                 135                 140

Ser Pro Leu Glu Val Ala Gln His Gly Pro Arg Ser Thr Gly Val Gly
145                 150                 155                 160

Ala Gln Ile Leu Gly Ala Ser Asp Lys Tyr Ile Cys Gln Tyr Ser Glu
                165                 170                 175

Glu Ser Gln Asn Phe Trp Gly Ser Arg His Glu Leu Met Leu Gly Asn
            180                 185                 190

Thr Phe Val Ala Glu Lys Gly Met Gln Pro Pro Ser Lys Glu Val Pro
        195                 200                 205

Pro Gln Glu Phe Asn Arg Met Val Ser Glu Gly Phe Gln Val Thr Pro
    210                 215                 220

Leu Trp Asn Gln Gly Phe Ile Arg Asp Asp Gly Arg Ser Asp Tyr Val
225                 230                 235                 240

Lys Thr Val Lys Thr Ala Arg Trp Glu Tyr Ser Thr Arg Pro Val Tyr
                245                 250                 255

Gly Trp Gly Asn Val Gly Ser Lys Gln Gln Ser Thr Ala Gly Trp Leu
            260                 265                 270

Ala Ala Phe Pro Val Phe Glu Pro His Trp Gln Ile Cys Met Ala Ala
        275                 280                 285

Gly Leu Ser Thr Gly Trp Ile Glu Trp Asp Gly Glu Arg Phe Glu Phe
    290                 295                 300

Lys Asp Ala Pro Ser Tyr Ser Glu Lys Asn Trp Gly Gly Gly Phe Pro
305                 310                 315                 320

Arg Lys Trp Phe Trp Ala Gln Cys Asn Thr Phe Glu Gly Ala Ser Gly
                325                 330                 335

Glu Val Ala Leu Thr Val Gly Gly Gly Leu Arg Gln Leu Pro Gly Leu
            340                 345                 350

Thr Glu Thr Phe Glu Asn Ala Ala Leu Ile Gly Val His Tyr Asp Gly
        355                 360                 365

Ile Phe Tyr Glu Phe Val Pro Trp Lys Gly Val Val Thr Trp Glu Ile
    370                 375                 380

Ser Pro Trp Gly Tyr Trp Phe Val Thr Ala Glu Asn Glu Thr His Leu
385                 390                 395                 400

Val Glu Leu Glu Ala Thr Thr Lys Asp Pro Gly Thr Thr Leu Arg Ala
                405                 410                 415

Pro Thr Thr Glu Ala Gly Leu Ala Pro Ala Cys Lys Asp Thr Cys Tyr
            420                 425                 430

Gly Val Leu Lys Leu Lys Leu Trp Glu Arg Arg Tyr Asp Gly Ser Lys
        435                 440                 445

Gly Lys Ile Ile Leu Asp Val Thr Ser Asp Met Ala Ala Val Glu Val
    450                 455                 460
```

-continued

```
Gly Gly Gly Pro Trp Phe Asn Thr Trp Lys Gly Lys Thr Thr Thr Pro
465                 470                 475                 480

Glu Leu Leu Ser Arg Ala Leu Arg Val Pro Leu Asp Val Asp Gly Ile
                485                 490                 495

Phe Asn Phe Leu Pro Leu Phe Lys Pro Pro Gly Leu
            500                 505


<210> SEQ ID NO 19
<211> LENGTH: 1408
<212> TYPE: DNA
<213> ORGANISM: Hevea brasiliensis

<400> SEQUENCE: 19

aagtgccatt acgctacccc atagcacagt gttccaccgt tcggttatcc cccacagttt      60

ctgtcatctc cagctctctc catgttgctg cagtgctact tatatccgcc ctcaatcctc     120

ccacaactcc gcacaaatct tcaatcctcg ctatttcttc ctactcgttg tcgtacttct     180

cacgctccgc tgctccgttc gatcaccgtc aaggcttcaa tatctactgt catggacgct     240

gacgctcaag tgaccttgct aaagaaaggc atagctgaac tgtatgacga gtcatctggt     300

atatgggaag ccttatgggg agaccacatg caccacgggt tctacgacac ggatgttaaa     360

gtttcgggct ctctttccga tcatagagct gctcagatcc gaatgatcga ggaggctctc     420

aggttcggca gcgttccaga ggacccaaaa aagtggccta agaacgtggt tgatgttggc     480

tgtgggattg gaggcagctc taggtacctg gcaaagaaat ttggggctca ttgccaaggc     540

atttctctca gtcctttcca agtccagagg gccaattctc tagcagctgc tgacggactg     600

gctgacaagg cttccttcca agttgcagat gctttagacc aaccatttcc agatgggcag     660

tttgatctgg tctggtcaat ggagagtgga gaacatatgc ctgacaaaag aaagtttgtt     720

agtgagttgg ctagagttgc agccccagga gccagaatta ttatagtaac atggtgccat     780

aggaacctca gcccttctga agaatctttg cagacatggg agaaagcaca tctgaagaag     840

atatgtgacg cttattatct tcctgaatgg tgttctgctg ctgattatgt tgaaatgctc     900

gagtctctct ctctacagga tattaaaaca gcagattggt ctcagaatgt ggcctctttt     960

tggccagcag tgattcgctc ggcattgact tggaagggct tgacttcact agtgcgtagt    1020

ggtctaaaaa ctattagagg agcattggtg atgccattga tgatccaagg ataccagaaa    1080

ggtcttatca agtttgccat cattacatgt cgaaagcctg aataaattta tagaaaggtt    1140

gaatgaacaa cagattgcgc agatatggca aagatcaaag gatttgaata aggatgacac    1200

tcactctttt agaagtttga gattaagctt atcatcatca ttacaagtaa aataattgaa    1260

taaggtatag tgattccatt gatgatccaa caaggataca agaaagacat attattagag    1320

aaaagggaat taaaaaatgg tggggagggg atatatttgt cacattatct acaatgacaa    1380

attatttaca accaaaaaaa aaaaaaaa                                        1408


<210> SEQ ID NO 20
<211> LENGTH: 347
<212> TYPE: PRT
<213> ORGANISM: Hevea brasiliensis

<400> SEQUENCE: 20

Met Leu Leu Gln Cys Tyr Leu Tyr Pro Pro Ser Ile Leu Pro Gln Leu
1               5                   10                  15

Arg Thr Asn Leu Gln Ser Ser Leu Phe Leu Pro Thr Arg Cys Arg Thr
            20                  25                  30
```

-continued

```
Ser His Ala Pro Leu Leu Arg Ser Ile Thr Val Lys Ala Ser Ile Ser
        35                  40                  45

Thr Val Met Asp Ala Asp Ala Gln Val Thr Leu Leu Lys Lys Gly Ile
    50                  55                  60

Ala Glu Leu Tyr Asp Glu Ser Ser Gly Ile Trp Glu Ala Leu Trp Gly
65                  70                  75                  80

Asp His Met His His Gly Phe Tyr Asp Thr Asp Val Lys Val Ser Gly
                85                  90                  95

Ser Leu Ser Asp His Arg Ala Ala Gln Ile Arg Met Ile Glu Glu Ala
            100                 105                 110

Leu Arg Phe Gly Ser Val Pro Glu Asp Pro Lys Lys Trp Pro Lys Asn
        115                 120                 125

Val Val Asp Val Gly Cys Gly Ile Gly Gly Ser Ser Arg Tyr Leu Ala
    130                 135                 140

Lys Lys Phe Gly Ala His Cys Gln Gly Ile Ser Leu Ser Pro Phe Gln
145                 150                 155                 160

Val Gln Arg Ala Asn Ser Leu Ala Ala Ala Asp Gly Leu Ala Asp Lys
                165                 170                 175

Ala Ser Phe Gln Val Ala Asp Ala Leu Asp Gln Pro Phe Pro Asp Gly
            180                 185                 190

Gln Phe Asp Leu Val Trp Ser Met Glu Ser Gly Glu His Met Pro Asp
        195                 200                 205

Lys Arg Lys Phe Val Ser Glu Leu Ala Arg Val Ala Ala Pro Gly Ala
    210                 215                 220

Arg Ile Ile Ile Val Thr Trp Cys His Arg Asn Leu Ser Pro Ser Glu
225                 230                 235                 240

Glu Ser Leu Gln Thr Trp Glu Lys Ala His Leu Lys Lys Ile Cys Asp
                245                 250                 255

Ala Tyr Tyr Leu Pro Glu Trp Cys Ser Ala Ala Asp Tyr Val Glu Met
            260                 265                 270

Leu Glu Ser Leu Ser Leu Gln Asp Ile Lys Thr Ala Asp Trp Ser Gln
        275                 280                 285

Asn Val Ala Ser Phe Trp Pro Ala Val Ile Arg Ser Ala Leu Thr Trp
    290                 295                 300

Lys Gly Leu Thr Ser Leu Val Arg Ser Gly Leu Lys Thr Ile Arg Gly
305                 310                 315                 320

Ala Leu Val Met Pro Leu Met Ile Gln Gly Tyr Gln Lys Gly Leu Ile
                325                 330                 335

Lys Phe Ala Ile Ile Thr Cys Arg Lys Pro Glu
            340                 345
```

HOMOGENTISIC ACID GERANYLGERANYL TRANSERASE POLYPEPTIDE

TECHNICAL FIELD

The present invention relates to enzymes participating in the vitamin E biosynthesis in Para rubber tree and the genes encoding the enzymes concerned.

BACKGROUND ART

The vitamin E is the most important natural antioxidant. The pathway for synthesis of the tocopherol in plant is described in detail later, for example, the pathway is mentioned in the literature of Collakova et al. (Collakova et al., Plant Physial., 133 (2003) p930-940) or the general remarks of Bowier et al. (Bowier et al., Progress in Lipid Res., 44 (2005) p414-416). In addition, as to the vitamin E of Para rubber tree, it is described that tocotrienol was isolated from Para rubber tree (*Hevea brasiliensis*) and identified in the literature of Whittle et al. (Whittle et al., Biochem. J., 100 (1966) p138-145) or the literature of Dunphy et al. (Dunphy et al., Nature, 207 (1965) p521-522).

As for the gene of enzyme derived from plant related to biosynthesis of the vitamin E, till now, the following examples are reported: the geranylgeranyl reductase derived from thale cress (*Arabidopsis thaliana*) was isolated (Keller et al., Eur. J. Biochem, 251 (1998) p413-417); the mutation of tocopherol cyclase gene caused to accumulate the precursor of 2,3-dimethyl-5-phytyl-1,4-benzoquinone into the leaves or seeds (Sattler et al., Plant Physiology, 132 (2003) p2184-2195 and Schledz et al., FEBS letter, 499 (2001) p15-20); the homogentisic acid geranylgeranyl transferase gene derived from barley was introduced into *Arabidopsis* or corn to be successful in control of the vitamin E content, composition (Cahoon et al., Nature Biotechnology, 21 (2003) p1082-1087), the γ-tocopherol methyl transferase gene derived from thale cress was introduced into thale cress to be successful in control of the vitamin E composition (Shintani et al., Science, 282 (1998) p2098-2100); the γ-tocopherol methyl transferase gene and the 2-methyl-6-phytyl benzoquinone methyl transferase gene derived from thale cress were introduced into soy bean to be successful in control of the vitamin E content, composition (Eenennaam et al., The Plant Cell, (2003) p3007-3019). In addition, as to the transgenic soy bean that the α-tocopherol content was raised, the patent application has been filed (Japanese Patent Application Laid-Open No. 2006-075106A bulletin). However, in the Para rubber tree, the gene of enzyme related to biosynthesis of the vitamin E was not acquired at all till now. Therefore, there was no means to control biosynthesis of the vitamin E in Para rubber tree till now.

Furthermore, FIG. 1 shows the biosynthetic pathway of the vitamin E of plant that has ever understood. Using prephenic acid as substrate, p-hydroxyphenyl pyruvic acid is generated by the action of prephenate dehydratase. And, by the action of p-hydroxyphenyl pyruvic acid dioxygenase, homogentisic acid is generated from p-hydroxyphenyl pyruvic acid. In addition, the nonmevalonate pathway acts on this synthesis, too, and phytyl diphosphate is generated from geranylgeranyl diphosphate by geranylgeranyl reductase.

From these products, benzoquinone derivative or plastoquinone derivative which is a precursor of the vitamin E is generated. In other words, from geranylgeranyl diphosphate and homogentisic acid, 2-methyl-6-geranylgeranyl benzoquinone is generated by the action of homogentisic acid geranylgeranyl transferase. In addition, from phytyl diphosphate and homogentisic acid, 2-methyl-6-phytyl benzoquinone is generated by the action of homogentisic acid phytyl transferase. Furthermore, from 2-methyl-6-geranylgeranyl benzoquinone and S-adenosyl-L-methionine, 2,3-dimethyl-5-geranylgeranyl-1,4-benzoquinone is generated by the action of 2-methyl-6-geranylgeranyl benzoquinone methyl transferase. In addition, from 2-methyl-6-phytyl benzoquinone and S-adenosyl-L-methionine, 2,3-dimethyl-5-phytyl-1,4-benzoquinone is generated by the action of 2-methyl-6-phytyl benzoquinone methyl transferase.

Tocotrienol is generated using them as raw materials. In other words, from 2,3-dimethyl-5-geranylgeranyl-1,4-benzoquinone, γ-tocotrienol is generated by the action of tocopherol cyclase, and from γ-tocotrienol and S-adenosyl-L-methionine, α-tocotrienol is generated by the action of γ-tocopherol methyl transferase. In addition, from 2-methyl-6-geranylgeranyl benzoquinone, δ-tocotrienol is generated by the action of tocopherol cyclase, and from δ-tocotrienol and S-adenosyl-L-methionine, β-tocotrienol is generated by the action of γ-tocopherol methyl transferase.

Furthermore, tocopherols are generated. In other words, from 2,3-dimethyl-5-phytyl-1,4-benzoquinone, γ-tocopherol is generated by the action of tocopherol cyclase, and from δ-tocopherol and S-adenosyl-L-methionine, α-tocopherol is generated by the action of γ-tocopherol methyl transferase. In addition, from 2-methyl-6-phytyl benzoquinone, δ-tocopherol is generated by the action of tocopherol cyclase, and from δ-tocopherol and S-adenosyl-L-methionine, β-tocopherol is generated by the action of γ-tocopherol methyl transferase.

DISCLOSURE OF INVENTION

However, the analysis concerning the gene group of the enzymes which involved in the biosynthesis of vitamin E in Para rubber tree (*Hevea brasiliensis*) was still insufficient till now. Therefore, it is a subject of this invention to isolate a gene group of enzymes involved in the biosynthesis of vitamin E of Para rubber tree, and to analyze base sequence of each gene constituting the gene group concerned.

Based on syntactic analysis of gene fragment information obtained by the EST (Expression Sequence Tags) analysis of Para rubber tree and the known gene database, the sequences which are assumed to be the gene cluster of enzymes involved in the biosynthesis of vitamin E were identified, and by full-length cDNA cloning, the gene homologs were obtained. Then the base sequences of each of the obtained genes were determined.

As mentioned above, the vitamin E is a well-known antioxidant, and it is confirmed that the vitamin E also acts on a rubber product as an antioxidant, namely an age resister (Malaika et al., Polymer & Composites, 8 (2000) p537). Therefore, practical plants having enhanced vitamin E content can be produced by transforming plants, especially rubber producing plants with the gene cluster of enzymes involved in the vitamin E biosynthesis and obtained by the present invention. More specifically, by preparing a transformed Para rubber tree obtained by introducing the genes of the present invention, it can be expected to cause a reinforcement of the biosynthesis of vitamin E, and consequently enhancing an age resister effect. Further herein, "to reinforce the biosynthesis of vitamin E" means that compared with natural plant, the biosynthesis of vitamin E is increased by introducing the gene of the invention into plants such as Para rubber trees or the like to be involved in the biosynthesis of vitamin E.

BRIEF DESCRIPTION OF DRAWINGS

FIG. 2 (SEQ ID NO:1) shows a base sequence of prephenate dehydratase.

FIG. 3 (SEQ ID NO:2) shows an amino acid sequence of prephenate dehydratase.

FIG. 4 (SEQ ID NO:3) shows a base sequence of prephenate dehydratase obtained from another clone.

FIG. 5 (SEQ ID NO:4) shows an amino acid sequence of prephenate dehydratase obtained from another clone.

FIG. 6 (SEQ ID NO:5) shows a base sequence of p-hydroxyphenyl pyruvic acid dioxygenase.

FIG. 7 (SEQ ID NO:6) shows an amino acid sequence of p-hydroxyphenyl pyruvic acid dioxygenase.

FIG. 8 (SEQ ID NO:7) shows a base sequence of geranylgeranyl reductase.

FIG. 9 (SEQ ID NO:8) shows an amino acid sequence of geranylgeranyl reductase.

FIG. 10 (SEQ ID NO:9) shows a base sequence of homogentisic acid phytyl transferase.

FIG. 11 (SEQ ID NO:10) shows an amino acid sequence of homogentisic acid phytyl transferase.

FIG. 12 (SEQ ID NO:11) shows a base sequence of 2-methyl-6-geranylgeranyl benzoquinone methyl transferase.

FIG. 13 (SEQ ID NO:12) shows an amino acid sequence of 2-methyl-6-geranylgeranyl benzoquinone methyl transferase.

FIG. 14 (SEQ ID NO:13) shows a base sequence of homogentisic acid geranylgeranyl transferase.

FIG. 15 (SEQ ID NO:14) shows an amino acid sequence of homogentisic acid geranylgeranyl transferase.

FIG. 16 (SEQ ID NO:15) shows a base sequence of 2-methyl-6-phytyl benzoquinone methyl transferase.

FIG. 17 (SEQ ID NO:16) shows an amino acid sequence of 2-methyl-6-phytyl benzoquinone methyl transferase.

FIG. 18 (SEQ ID NO:17) shows a base sequence of tocopherol cyclase.

FIG. 19 (SEQ ID NO:18) shows an amino acid sequence of tocopherol cyclase.

FIG. 20 (SEQ ID NO:19) shows a base sequence of γ-tocopherol methyl transferase.

FIG. 21 (SEQ ID NO:20) shows an amino acid sequence of γ-tocopherol methyl transferase.

BEST MODE FOR CARRYING OUT THE INVENTION

Figure 1:
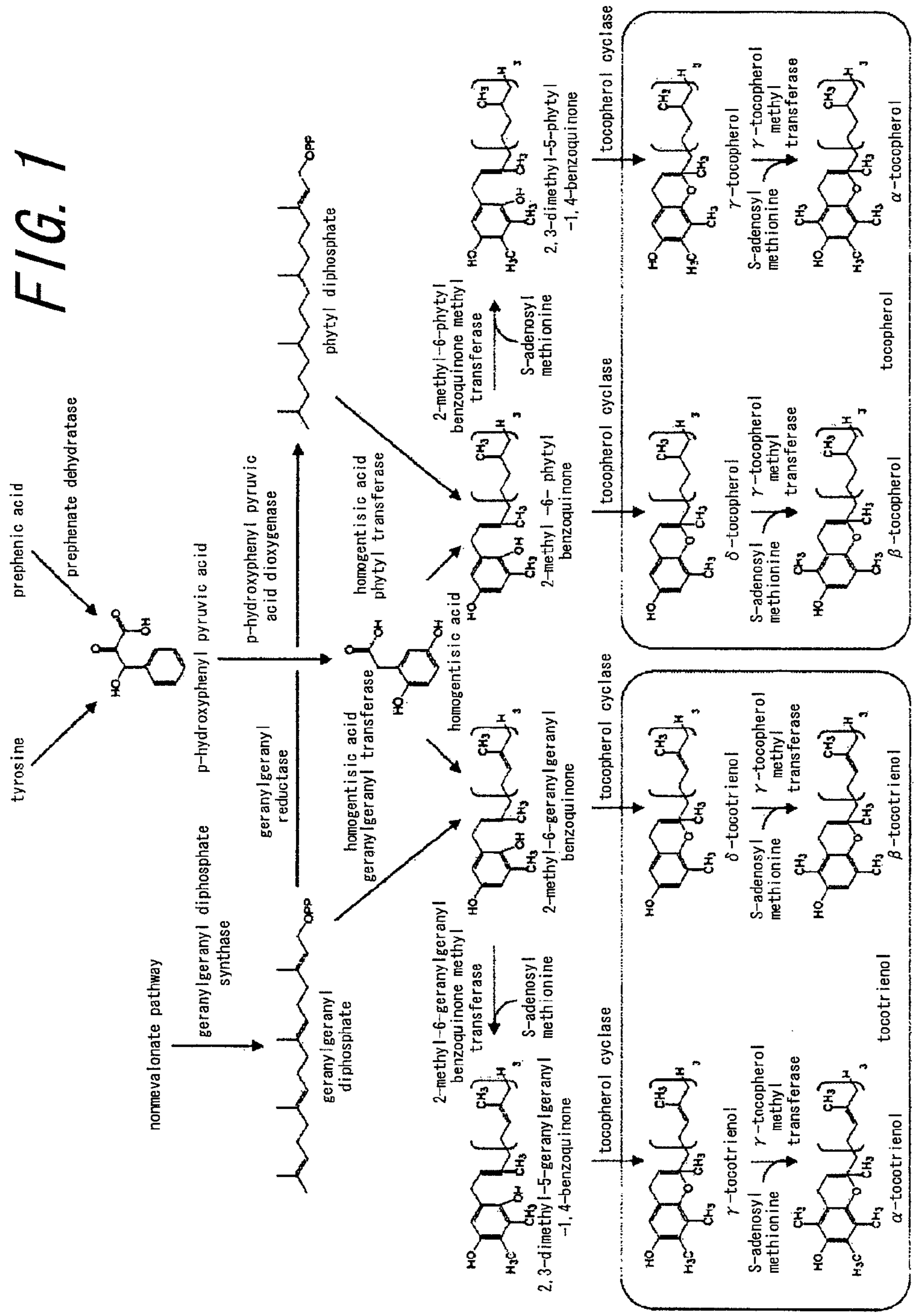
FIG. 1 shows the vitamin E biosynthesis pathway of plant.

As for the emulsion (Latex) of Para rubber tree standard tree and wood tissue (Xylem) of the current year branch, total RNA was extracted and cDNA libraries were prepared. Exhaustive one-pass sequence analysis was performed on these libraries. Then 16407 EST sequences were obtained from the cDNA library prepared from the latex and 16305 EST sequences from the cDNA library were obtained from the xylem with high accuracy (Total 32442). On the obtained partial sequences, clustering analysis based on similarity between sequences and annotation analysis based on comparison with known genes were performed, and thus an EST database of Para rubber tree (*Hevea brasiliensis*) was constructed.

In the obtained EST database, the inventors have found EST sequences which are thought to encode a prephenate dehydratase, another prephenate dehydratase obtained from other clone, p-hydroxyphenyl pyruvic acid dioxygenase, geranylgeranyl reductase, homogentisic acid phytyl transferase, 2-methyl-6-geranylgeranyl benzoquinone methyl transferase, 2-methyl-6-phytyl benzoquinone methyl transferase. As for these sequences, the inventors have determined the 3'-terminal sequence by 3'-RACE (Rapid Amplification of cDNA Ends) and obtained full-length cDNAs.

In addition, as to homogentisic acid geranylgeranyl transferase, tocopherol cyclase, γ-tocopherol methyl transferase which were not found in EST database among various enzymes of the vitamin E biosynthesis pathway, by the alignment of known amino acid sequences of other plants, the degeneration of primer (Degenerate Primer) is designed from the high conservation region, and a partial sequence of the reading frame (ORF) is acquired by PCR. Furthermore, based on the obtained each partial sequence information, the inventors have determined the 3'-terminal sequence by 3'-RACE and the 5'-terminal sequence by 5'-RACE and obtained full-length cDNAs.

A base sequence of gene encoding prephenate dehydratase is represented by base numbers from 1 to 1677 in the nucleotide sequence of FIG. 2 and SEQ ID NO: 1 in the sequence list. The part corresponding to base numbers from 160 to 1329 in the base sequence in SEQ ID NO: 1 in the sequence list corresponds to the open reading frame. A deduced amino acid sequence of prephanate dehydratase obtained from the base sequence of the open reading frame is represented by amino acid numbers from 1 to 390 in FIG. 3 and SEQ ID NO: 2 in the sequence list. Meanwhile, the prephanate dehydratase is an enzyme that catalyzes the reaction which biosynthesizes p-hyroxyphenyl pyruvic acid using prephenic acid as a substrate.

A base sequence of gene encoding prephenate dehydratase obtained from another clone is represented by base numbers from 1 to 1760 in the nucleotide sequence of FIG. 4 and SEQ ID NO: 3 in the sequence list. The part corresponding to base numbers from 199 to 1485 in the base sequence in SEQ ID NO: 3 in the sequence list corresponds to the open reading frame. A deduced amino acid sequence of prephanate dehydratase obtained from the base sequence of the open reading frame is represented by amino acid numbers from 1 to 429 in FIG. 5 and SEQ ID NO: 4 in the sequence list. Meanwhile, as mentioned above, the prephanate dehydratase is an enzyme that catalyzes the reaction which biosynthesizes p-hyroxyphenyl pyruvic acid using prephenic acid as a substrate.

A base sequence of gene encoding p-hydroxyphenyl pyruvic acid dioxygenase is represented by base numbers from 1 to 1631 in the nucleotide sequence of FIG. 6 and SEQ ID NO: 5 in the sequence list. The part corresponding to base numbers from 47 to 1381 in the base sequence in SEQ ID NO: 5 in the sequence list corresponds to the open reading frame. A deduced amino acid sequence of p-hydroxyphenyl pyruvic acid dioxygenase from the base sequence of the open reading frame is represented by amino acid numbers from 1 to 445 in FIG. 7 and SEQ ID NO: 6 in the sequence list. Meanwhile, the p-hydroxyphenyl pyruvic acid dioxygenase is an enzyme that catalyzes the reaction which biosynthesizes homogentisic acid using p-hydroxyphenyl pyruvic acid as a substrate.

A base sequence of gene encoding geranylgeranyl reductase is represented by base numbers from 1 to 1793 in the nucleotide sequence of FIG. 8 and SEQ ID NO: 7 in the sequence list. The part corresponding to base numbers from 12 to 1424 in the base sequence in SEQ ID NO: 7 in the sequence list corresponds to the open reading frame. A deduced amino acid sequence of geranylgeranyl reductase obtained from the base sequence of the open reading frame is represented by amino acid numbers from 1 to 471 in FIG. 9 and SEQ ID NO: 8 in the sequence list. Meanwhile, the geranylgeranyl reductase is an enzyme that catalyzes the reaction which biosynthesizes phytyl diphosphate using geranylgeranyl diphosphate as a substrate.

A base sequence of gene encoding homogentisic acid phytyl transferase is represented by base numbers from 1 to 1563 in the nucleotide sequence of FIG. 10 and SEQ ID NO: 9 in the sequence list. The part corresponding to base numbers from 93 to 1334 in the base sequence in SEQ ID NO: 9 in the sequence list corresponds to the open reading frame. A deduced amino acid sequence of homogentisic acid phytyl transferase obtained from the base sequence of the open reading frame is represented by amino acid numbers from 1 to 414 in FIG. 11 and SEQ ID NO: 10 in the sequence list. Meanwhile, the homogentisic acid phytyl transferase is an enzyme that catalyzes the reaction which biosynthesizes 2-methyl-6-phytyl benzoquinone using homogentisic acid and phytyl diphosphate as substrate.

A base sequence of gene encoding 2-methyl-6-geranylgeranyl benzoquinone methyl transferase is represented by base numbers from 1 to 1410 in the nucleotide sequence of FIG. 12 and SEQ ID NO: 11 in the sequence list. The part corresponding to base numbers from 165 to 1187 in the base sequence in SEQ ID NO: 11 in the sequence list corresponds to the open reading frame. A deduced amino acid sequence of 2-methyl-6-geranylgeranyl benzoquinone methyl transferase obtained from the base sequence of the open reading frame is represented by amino acid numbers from 1 to 341 in FIG. 13 and SEQ ID NO: 12 in the sequence list. Meanwhile, the 2-methyl-6-geranylgeranyl benzoquinone methyl transferase is an enzyme that catalyzes the reaction which biosynthesizes 2,3-dimethyl-5-geranylgeranyl-1,4-benzoquinone using 2-methyl-6-geranylgeranyl benzoquinone and S-adenosyl-L-methionine as substrate.

A base sequence of gene encoding homogentisic acid geranylgeranyl transferase is represented by base numbers from 1 to 1837 in the nucleotide sequence of FIG. 14 and SEQ ID NO: 13 in the sequence list. The part corresponding to base numbers from 82 to 1317 in the base sequence in SEQ ID NO: 13 in the sequence list corresponds to the open reading frame. A deduced amino acid sequence of homogentisic acid geranylgeranyl transferase obtained from the base sequence of the open reading frame is represented by amino acid numbers from 1 to 411 in FIG. 15 and SEQ ID NO: 14 in the sequence list. Meanwhile, the homogentisic acid geranylgeranyl transferase is an enzyme that catalyzes the reaction which biosynthesizes 2-methyl-6-geranylgeranyl benzoquinone using geranylgeranyl diphosphate and homogentisic acid as substrate.

A base sequence of gene encoding 2-methyl-6-phytyl benzoquinone methyl transferase is represented by base numbers from 1 to 1282 in the nucleotide sequence of FIG. 16 and SEQ ID NO: 15 in the sequence list. The part corresponding to base numbers from 84 to 1106 in the base sequence in SEQ ID NO: 15 in the sequence list corresponds to the open reading frame. A deduced amino acid sequence of 2-methyl-6-phytyl benzoquinone methyl transferase obtained from the base sequence of the open reading frame is represented by amino acid numbers from 1 to 340 in FIG. 17 and SEQ ID NO: 16 in the sequence list. Meanwhile, the 2-methyl-6-phytyl benzoquinone methyl transferase is an enzyme that catalyzes the reaction which biosynthesizes 2,3-dimethyl-5-phytyl-1,4-benzoquinone using 2-methyl-6-phytyl benzoquinone and S-adenosyl-L-methionine as substrate.

A base sequence of gene encoding tocopherol cyclase is represented by base numbers from 1 to 2008 in the nucleotide sequence of FIG. 18 and SEQ ID NO: 17 in the sequence list. The part corresponding to base numbers from 123 to 1649 in the base sequence in SEQ ID NO: 17 in the sequence list corresponds to the open reading frame. A deduced amino acid sequence of tocopherol cyclase obtained from the base sequence of the open reading frame is represented by amino acid numbers from 1 to 508 in FIG. 19 and SEQ ID NO: 18 in the sequence list. Meanwhile, the tocopherol cyclase is an enzyme that catalyzes the reaction which biosynthesizes tocotrienols or tocopherols using benzoquinone derivative or plastoquinone derivative of precursor for the vitamin E as substrate.

A base sequence of gene encoding γ-tocopherol methyl transferase is represented by base numbers from 1 to 1408 in the nucleotide sequence of FIG. 20 and SEQ ID NO: 19 in the sequence list. The part corresponding to base numbers from 82 to 1125 in the base sequence in SEQ ID NO: 19 in the sequence list corresponds to the open reading frame. A deduced amino acid sequence of γ-tocopherol methyl transferase obtained from the base sequence of the open reading frame is represented by amino acid numbers from 1 to 347 in FIG. 21 and SEQ ID NO: 20 in the sequence list. Meanwhile, the γ-tocopherol methyl transferase is an enzyme that catalyzes the reaction which biosynthesizes β-tocopherol or β-tocotrienol using δ-tocopherol or δ-tocotrienol and S-adenosyl-L-methionine as substrate, or α-tocopherol or α-tocotrienol using γ-tocopherol or γ-tocotrienol and S-adenosyl-L-methionine as substrate.

According to gene recombination technology, artificial mutation can be made to a particular site of the original DNA, without changing the fundamental properties of the DNA or in such a way as to improve these properties. As for genes having natural base sequences provided according to the present invention or even genes having base sequences different from the natural sequence, artificial insertion, deletion and substitution can be performed in the same manner, and they can be altered to have an equal or improved properties as the natural genes. Moreover, the present invention includes such mutated genes.

Specifically, a gene consisting of a base sequence in which a part of the nucleotide sequence shown in SEQ ID NO: 1 in the sequence list has been deleted, substituted or added means a gene in which no more than 20, preferably no more than 10, more preferably no more than 5 base sequences in the nucleotide sequence in SEQ ID NO: 1 have been substituted. Furthermore, such a gene has no less than 95%, preferably no less than 97%, more preferably no less than 99% homology with the nucleotide sequence shown in SEQ ID NO: 1. Even such a gene is also within the scope of the present invention, as long as the gene encodes a protein having the function as prephenate dehydratase, which biosynthesizes p-hydroxyphenyl pyruvic acid using prephenic acid as a substrate. Additionally, such a gene hybridizes with the gene shown in SEQ ID NO: 1 in the sequence list under stringent conditions.

Similarly, a gene consisting of a base sequence in which a part of the nucleotide sequence shown in SEQ ID NO: 3 in the sequence list has been deleted, substituted or added means a gene in which no more than 20, preferably no more than 10, more preferably no more than 5 base sequences in the nucleotide sequence in SEQ ID NO: 3 have been substituted. Furthermore, such a gene has no less than 95%, preferably no less than 97%, more preferably no less than 99% homology with the nucleotide sequence shown in SEQ ID NO: 3. Even such a gene is also within the scope of the present invention, as long as the gene encodes a protein having the function as prephenate dehydratase, which biosynthesizes p-hydroxyphenyl pyruvic acid using prephenic acid as a substrate. Additionally, such a gene hybridizes with the gene shown in SEQ ID NO: 3 in the sequence list under stringent conditions.

Similarly, a gene consisting of a base sequence in which a part of the nucleotide sequence shown in SEQ ID NO: 5 in the sequence list has been deleted, substituted or added means a gene in which no more than 20, preferably no more than 10, more preferably no more than 5 base sequences in the nucleotide sequence in SEQ ID NO: 5 have been substituted. Furthermore, such a gene has no less than 95%, preferably no less than 97%, more preferably no less than 99% homology with the nucleotide sequence shown in SEQ ID NO: 5. Even such a gene is also within the scope of the present invention, as long as the gene encodes a protein having the function as p-hydroxyphenyl pyruvic acid dioxygenase, which biosynthesizes homogentisic acid using p-hydroxyphenyl pyruvic acid as a substrate. Additionally, such a gene hybridizes with the gene shown in SEQ ID NO: 5 in the sequence list under stringent conditions.

Similarly, a gene consisting of a base sequence in which a part of the nucleotide sequence shown in SEQ ID NO: 7 in the sequence list has been deleted, substituted or added means a gene in which no more than 20, preferably no more than 10, more preferably no more than 5 base sequences in the nucleotide sequence in SEQ ID NO: 7 have been substituted. Furthermore, such a gene has no less than 95%, preferably no less than 97%, more preferably no less than 99% homology with the nucleotide sequence shown in SEQ ID NO: 7. Even such a gene is also within the scope of the present invention, as long as the gene encodes a protein having the function as geranylgeranyl reductase, which biosynthesizes phytyl diphosphate using geranylgeranyl diphosphate as a substrate. Additionally, such a gene hybridizes with the gene shown in SEQ ID NO: 7 in the sequence list under stringent conditions.

Similarly, a gene consisting of a base sequence in which a part of the nucleotide sequence shown in SEQ ID NO: 9 in the sequence list has been deleted, substituted or added means a gene in which no more than 20, preferably no more than 10, more preferably no more than 5 base sequences in the nucleotide sequence in SEQ ID NO: 9 have been substituted. Furthermore, such a gene has no less than 95%, preferably no less than 97%, more preferably no less than 99% homology with the nucleotide sequence shown in SEQ ID NO: 9. Even such a gene is also within the scope of the present invention, as long as the gene encodes a protein having the function as homogentisic acid phytyl transferase, which biosynthesizes 2-methyl-6-phytyl benzoquinone using homogentisic acid and phytyl diphosphate as substrate. Additionally, such a gene hybridizes with the gene shown in SEQ ID NO: 9 in the sequence list under stringent conditions.

Similarly, a gene consisting of a base sequence in which a part of the nucleotide sequence shown in SEQ ID NO: 11 in the sequence list has been deleted, substituted or added means a gene in which no more than 20, preferably no more than 10, more preferably no more than 5 base sequences in the nucleotide sequence in SEQ ID NO: 11 have been substituted. Furthermore, such a gene has no less than 95%, preferably no less than 97%, more preferably no less than 99% homology with the nucleotide sequence shown in SEQ ID NO: 11. Even such a gene is also within the scope of the present invention; as long as the gene encodes a protein having the function as 2-methyl-6-geranylgeranyl benzoquinone methyl transferase, which biosynthesizes 2,3-dimethyl-5-geranylgeranyl-1,4-benzoquinone using 2-methyl-6-geranylgeranyl benzoquinone and S-adenosyl-L-methionine as substrate. Additionally, such a gene hybridizes with the gene shown in SEQ ID NO: 11 in the sequence list under stringent conditions.

Similarly, a gene consisting of a base sequence in which a part of the nucleotide sequence shown in SEQ ID NO: 13 in the sequence list has been deleted, substituted or added means a gene in which no more than 20, preferably no more than 10, more preferably no more than 5 base sequences in the nucleotide sequence in SEQ ID NO: 13 have been substituted. Furthermore, such a gene has no less than 95%, preferably no less than 97%, more preferably no less than 99% homology with the nucleotide sequence shown in SEQ ID NO: 13. Even such a gene is also within the scope of the present invention, as long as the gene encodes a protein having the function as homogentisic acid geranylgeranyl transferase, which biosynthesizes 2-methyl-6-geranylgeranyl benzoquinone using geranylgeranyl diphosphate and homogentisic acid as substrate. Additionally, such a gene hybridizes with the gene shown in SEQ ID NO: 13 in the sequence list under stringent conditions.

Similarly, a gene consisting of a base sequence in which a part of the nucleotide sequence shown in SEQ ID NO: 15 in the sequence list has been deleted, substituted or added means a gene in which no more than 20, preferably no more than 10, more preferably no more than 5 base sequences in the nucleotide sequence in SEQ ID NO: 15 have been substituted. Furthermore, such a gene has no less than 95%, preferably no less than 97%, more preferably no less than 99% homology with the nucleotide sequence shown in SEQ ID NO: 15. Even such a gene is also within the scope of the present invention, as long as the gene encodes a protein having the function as 2-methyl-6-phytyl benzoquinone methyl transferase, which biosynthesizes 2,3-dimethyl-5-phytyl-1,4-benzoquinone using 2-methyl-6-phytyl benzoquinone and S-adenosyl-L-methionine as substrate. Additionally, such a gene hybridizes with the gene shown in SEQ ID NO: 15 in the sequence list under stringent conditions.

Similarly, a gene consisting of a base sequence in which a part of the nucleotide sequence shown in SEQ ID NO: 17 in the sequence list has been deleted, substituted or added means a gene in which no more than 20, preferably no more than 10, more preferably no more than 5 base sequences in the nucleotide sequence in SEQ ID NO: 17 have been substituted. Furthermore, such a gene has no less than 95%, preferably no less than 97%, more preferably no less than 99% homology with the nucleotide sequence shown in SEQ ID NO: 17. Even such a gene is also within the scope of the present invention, as long as the gene encodes a protein having the function as tocopherol cyclase, which biosynthesizes tocotrienols or tocopherols using benzoquinone derivative or plastoquinone derivative of precursor for the vitamin E as substrate. Additionally, such a gene hybridizes with the gene shown in SEQ ID NO: 17 in the sequence list under stringent conditions.

Similarly, a gene consisting of a base sequence in which a part of the nucleotide sequence shown in SEQ ID NO: 19 in the sequence list has been deleted, substituted or added means a gene in which no more than 20, preferably no more than 10, more preferably no more than 5 base sequences in the nucleotide sequence in SEQ ID NO: 19 have been substituted. Furthermore, such a gene has no less than 95%, preferably no less than 97%, more preferably no less than 99% homology with the nucleotide sequence shown in SEQ ID NO: 19. Even such a gene is also within the scope of the present invention, as long as the gene encodes a protein having the function as γ-tocopherol methyl transferase, which biosynthesizes β-tocopherol or β-tocotrienol using δ-tocopherol or δ-tocotrienol and S-adenosyl-L-methionine as substrate, or α-tocopherol or α-tocotrienol using γ-tocopherol or γ-tocotrienol and S-adenosyl-L-methionine as substrate. Additionally, such a gene hybridizes with the gene shown in SEQ ID NO: 19 in the sequence list under stringent conditions.

Those skilled in the art may select conditions for hybridization ad libitum. The hybridization can be concretely performed by the following operations. A membrane onto which a DNA or RNA molecule to be tested has been transferred and a labeled probe can be hybridized in an applicable hybridization buffer. The hybridization buffer may be composed of 5×SSC, 0.1% by mass N-lauroyl sarcosine, 0.02% by mass SDS, 2% by mass blocking reagent for nucleic acid hybridization, and 50% by mass formamide, for instance. As the blocking reagent for nucleic acid hybridization, by way of example, commercially available blocking reagent for nucleic acid hybridization can be dissolved into a buffer solution (pH 7.5) composed of 0.1 M maleic acid and 0.15 M NaCl to make the concentration of the blocking reagent to be 10%. 20×SSC may be composed of 3 M NaCl and 0.3 M citric acid solution. SSC may be used preferably at 3 to 6×SSC concentration, and more preferably at 4 to 5×SSC concentration.

Hybridization may be performed at 40 to 80° C., preferably at 50 to 70° C., and more preferably at 55 to 65° C. Washing may be performed using a washing buffer after incubation for several hours or overnight. Washing may be performed preferably at room temperature, and more preferably at the temperature of hybridization. The washing buffer may be composed of 6×SSC+0.1% by mass SDS solution, preferably composed of 4×SSC+0.1% by mass SDS solution, more preferably composed of 2×SSC+0.1% by mass SDS solution, even more preferably composed of 1×SSC+0.1% by mass SDS solution, and most preferably composed of 0.1×SSC+0.1% by mass SDS solution. The membrane can be washed with such a washing buffer and the DNA molecule or RNA molecule hybridized with the probe can be identified by the label used for the probe.

Further herein, a protein consisting of an amino acid sequence in which a part of the amino acid sequence shown in SEQ ID NO: 2 has been deleted, substituted or added means a protein in which no more than 20, preferably no more than 10, more preferably no more than 5 amino acids in the amino acid sequence in SEQ ID NO: 2 have been substituted. Further, such a protein has no less than 95%, preferably no less than 97%, more preferably no less than 99% homology with the amino acid sequence shown in SEQ ID NO: 2. Even such a protein is within the scope of the present invention, as long as the protein has the function as prephenate dehydratase, which biosynthesizes p-hydroxyphenyl pyruvic acid using prephenic acid as substrate.

Similarly, a protein consisting of an amino acid sequence in which a part of the amino acid sequence shown in SEQ ID NO: 4 has been deleted, substituted or added means a protein in which no more than 20, preferably no more than 10, more preferably no more than 5 amino acids in the amino acid sequence in SEQ ID NO: 4 have been substituted. Further, such a protein has no less than 95%, preferably no less than 97%, more preferably no less than 99% homology with the amino acid sequence shown in SEQ ID NO: 4. Even such a protein is within the scope of the present invention, as long as the protein has the function as prephenate dehydratase, which biosynthesizes p-hydroxyphenyl pyruvic acid using prephenic acid as substrate.

Similarly, a protein consisting of an amino acid sequence in which a part of the amino acid sequence shown in SEQ ID NO: 6 has been deleted, substituted or added means a protein in which no more than 20, preferably no more than 10, more preferably no more than 5 amino acids in the amino acid sequence in SEQ ID NO: 6 have been substituted. Further, such a protein has no less than 95%, preferably no less than 97%, more preferably no less than 99% homology with the amino acid sequence shown in SEQ ID NO: 6. Even such a protein is within the scope of the present invention, as long as the protein has the function as p-hydroxyphenyl pyruvic acid dioxygenase, which biosynthesizes homogentisic acid using p-hydroxyphenyl pyruvic acid as substrate.

Similarly, a protein consisting of an amino acid sequence in which a part of the amino acid sequence shown in SEQ ID NO: 8 has been deleted, substituted or added means a protein in which no more than 20, preferably no more than 10, more preferably no more than 5 amino acids in the amino acid sequence in SEQ ID NO: 8 have been substituted. Further, such a protein has no less than 95%, preferably no less than 97%, more preferably no less than 99% homology with the amino acid sequence shown in SEQ ID NO: 8. Even such a protein is within the scope of the present invention, as long as the protein has the function as geranylgeranyl reductase, which biosynthesizes phytyl diphosphate using geranylgeranyl diphosphate as substrate.

Similarly, a protein consisting of an amino acid sequence in which a part of the amino acid sequence shown in SEQ ID NO: 10 has been deleted, substituted or added means a protein in which no more than 20, preferably no more than 10, more preferably no more than 5 amino acids in the amino acid sequence in SEQ ID NO: 10 have been substituted. Further, such a protein has no less than 95%, preferably no less than 97%, more preferably no less than 99% homology with the amino acid sequence shown in SEQ ID NO: 10. Even such a protein is within the scope of the present invention, as long as the protein has the function as homogentisic acid phytyl transferase, which biosynthesizes 2-methyl-6-phytyl benzoquinone using homogentisic acid and phytyl diphosphate as substrate.

Similarly, a protein consisting of an amino acid sequence in which a part of the amino acid sequence shown in SEQ ID NO: 12 has been deleted, substituted or added means a protein in which no more than 20, preferably no more than 10, more preferably no more than 5 amino acids in the amino acid sequence in SEQ ID NO: 12 have been substituted. Further, such a protein has no less than 95%, preferably no less than 97%, more preferably no less than 99% homology with the amino acid sequence shown in SEQ ID NO: 12. Even such a protein is within the scope of the present invention, as long as the protein has the function as 2-methyl-6-geranylgeranyl benzoquinone methyl transferase, which biosynthesizes 2,3-dimethyl-5-geranylgeranyl-1,4-benzoquinone using 2-methyl-6-geranylgeranyl benzoquinone and S-adenosyl-L-methionine as substrate.

Similarly, a protein consisting of an amino acid sequence in which a part of the amino acid sequence shown in SEQ ID NO: 14 has been deleted, substituted or added means a protein in which no more than 20, preferably no more than 10, more preferably no more than 5 amino acids in the amino acid sequence in SEQ ID NO: 14 have been substituted. Further, such a protein has no less than 95%, preferably no less than 97%, more preferably no less than 99% homology with the amino acid sequence shown in SEQ ID NO: 14. Even such a protein is within the scope of the present invention, as long as the protein has the function as homogentisic acid geranylgeranyl transferase, which biosynthesizes 2-methyl-6-geranylgeranyl benzoquinone using geranylgeranyl diphosphate and homogentisic acid as substrate.

Similarly, a protein consisting of an amino acid sequence in which a part of the amino acid sequence shown in SEQ ID NO: 16 has been deleted, substituted or added means a protein in which no more than 20, preferably no more than 10, more preferably no more than 5 amino acids in the amino acid sequence in SEQ ID NO: 16 have been substituted. Further, such a protein has no less than 95%, preferably no less than 97%, more preferably no less than 99% homology with the amino acid sequence shown in SEQ ID NO: 16. Even such a protein is within the scope of the present invention, as long as the protein has the function as 2-methyl-6-phytyl benzoquinone methyl transferase, which biosynthesizes 2,3-dimethyl-5-phytyl-1,4-benzoquinone using 2-methyl-6-phytyl benzoquinone and S-adenosyl-L-methionine as substrate.

Similarly, a protein consisting of an amino acid sequence in which a part of the amino acid sequence shown in SEQ ID NO: 18 has been deleted, substituted or added means a protein in which no more than 20, preferably no more than 10, more preferably no more than 5 amino acids in the amino acid sequence in SEQ ID NO: 18 have been substituted. Further, such a protein has no less than 95%, preferably no less than 97%, more preferably no less than 99% homology with the amino acid sequence shown in SEQ ID NO: 18. Even such a protein is within the scope of the present invention, as long as the protein has the function as tocopherol cyclase, which biosynthesizes tocotrienols or tocopherols using benzoquinone derivative or plastoquinone derivative of precursor for the vitamin E as substrate.

Similarly, a protein consisting of an amino acid sequence in which a part of the amino acid sequence shown in SEQ ID NO: 20 has been deleted, substituted or added means a protein in which no more than 20, preferably no more than 10, more preferably no more than 5 amino acids in the amino acid sequence in SEQ ID NO: 20 have been substituted. Further, such a protein has no less than 95%, preferably no less than 97%, more preferably no less than 99% homology with the amino acid sequence shown in SEQ ID NO: 20. Even such a protein is within the scope of the present invention, as long as the protein has the function as γ-tocopherol methyl transferase, which biosynthesizes β-tocopherol or β-tocotrienol using δ-tocopherol or δ-tocotrienol and S-adenosyl-L-methionine as substrate, or α-tocopherol or α-tocotrienol using γ-tocopherol or γ-tocotrienol and S-adenosyl-L-methionine as substrate.

The gene cluster encoding enzymes of the present invention involved in the biosynthesis of vitamin E can be introduced into plants such as rubber tree to enhance its expression, so that the expression level of the enzymes can be increased in said plants. Specifically, a transformed rubber tree can be prepared by introducing the gene encoding enzyme involved in the biosynthesis of vitamin E obtained in the present invention, so that the vitamin E content can be increased in the emulsion (Latex), especially. Consequently, due to the antioxidant effect of the vitamin E, it can be expected to enhance the age resister effect of rubber.

The plant to be introduced with gene of the present invention is not limited to Para rubber tree (*Hevea brasiliensis*), the examples of other plants may be *Periploca*, guayule, cassava, sunflower, lettuce, Indian rubber tree, and etc., but the target plants to be transformed are not limited to these plants, and transformants into which the gene of the present invention has been introduced can be produced in various plants. Among others, according to this invention, it is preferable to transform rubber-producing plants, such as *Hevea brasiliensis*. Particularly, the expression of gene of this invention can be reinforced in the rubber-producing plants, latex tube to increase the expression of enzyme of this invention involved in the biosynthesis of vitamin E, so that the vitamin E content can be increased in the emulsion (Latex) produced from the latex tube, thereby increasing the vitamin E content in the rubber obtained from said rubber-producing plants. Rubber-producing plants are known to spread wide variety of families that the plants biosynthesize 2,3-dimethyl-5-phytyl-1,4-benzoquinone using 2-methyl-6-phytyl benzoquinone and S-adenosyl-L-methionine as substrate, including Asteraceae, Moraceae, Euphorbiaceae, Asclepiadaceae, Apocynaceae, Sapotaceae and the like.

As a method for producing transformants, usual methods known in the art can be used. As an useful promoter for activating the introduced gene, the cauliflower mosaic virus 35S promoter widely used in the art, for example, can be used and positioned upstream of the gene of the present invention, which is to be transduced. In many cases, some promoter is required to achieve sufficient expression of the introduced foreign gene. The preferred promoter is not limited to the cauliflower mosaic virus 35S promoter, and various promoters widely used in the art may also be used. Furthermore, in order to increase the yield of rubber, it is preferable to use a promoter specific for the latex tube.

Furthermore, the vectors which can be used in the present invention may include, but not limited to, vectors such as pIG121-Hm, pBI12, pBI221, pBIN19, pCC22, pGA482, pPCV001, pCGN1547, pJJ1881, pPZP111, pGreen0029, pBI101, pBI121, pYLTAC7 and the like. Transgenic plants can be prepared by introducing such vectors into *Agrobacterium*, for instance, to have a callus or a seedling infected, and thus seeds derived from such transgenic plants can be obtained. Further, the transformation method for introducing the plant gene of the present invention into plants is not limited to the *Agrobacterium* method, but various methods commonly used in the art including the particle gun method and the electroporation method and the like may also be used. Additionally, an example in which a foreign gene is introduced into rubber tree for transformation is disclosed in Japanese Patent Application Laid-Open No. Hei. 8-116977. Therefore, those skilled in the art can produce a transgenic plant, into which the gene of the present invention has been introduced, by making appropriate alterations with reference to the description of Japanese Patent Application Laid-Open No. Hei. 8-116977.

EXAMPLES

Materials

Latex and xylem collected from the current year branch of Para rubber tree (*Hevea brasiliensis*) PRIM 600 standard tree cultivated in Cikampek, Indonesia were used as a plant sample. The latex was suspended in an equal amount of 2× sampling buffer (0.1 M Tris-HCL, 0.3 M LiCl, 0.01 M EDTA, 10% SDS) immediately after sampling the latex. *Periploca* (*Periploca sepium* Bunge) was gifted from Yoshihisa Nakazawa, Hitachi Zosen Corporation.

(RNA Extraction from Para Rubber Tree)

RNA was extracted from the latex and xylem respectively by the following procedures. Immediately after sampling, the sample (equivalent to 25 ml of latex) suspended in an equal amount of 2× sampling buffer (0.1 M Tris-HCL, 0.3 M LiCl, 0.01 M EDTA, 10% SDS) was centrifuged, and the upper layer constituting the rubber layer was removed. Then, 1.5 equivalent amount of 2×CTAB solution (2% hexadecyltrimethylammonium bromide (CTAB), 1% 2-mercaptoethanol, 0.1 M Tris-HCl (pH9.5), 1.4 M NaCl, 20 mM EDTA) was added and incubation was carried out at 65° C. for 10 minutes.

Moreover, an equal amount of chloroform/isoamyl alcohol was added. After obtaining the suspension, an aqueous layer was collected by centrifugation. Again, an equal amount of chloroform/isoamyl alcohol was added. After obtaining the suspension, an aqueous layer was collected by centrifugation. A quarter (¼) amount of 10 M LiCl was added and mixed, then incubated at −20° C. for 2 hours (selective precipitation of RNA). It was centrifuged, the precipitation was dissolved into an appropriate amount of TE, then centrifuged, and the supernatant was collected (polysaccharides were removed). Further, the fraction was treated with phenol, phenol/chloroform, chloroform/isoamyl alcohol, and then selective precipitation of RNA by LiCl was performed again. The precipitation was rinsed with 70% ethanol, and dissolved in DEPC-treated water after being dried under reduced pressure. Thus, total RNA derived from latex was obtained.

Also, from the current year branch, the phloem tissue was peeled off by a knife to obtain about 1 g of xylem tissue, and it was fractured in a mortar with a pestle while cooling with liquid nitrogen. The total RNA derived from xylem was obtained using RNeasy (registered trademark) Plant Mini Kit (QIAGEN). The obtained RNA solution was quantified by absorbance determination, and this was confirmed by electrophoresis. A 450 μg of RNA was obtained from 25 ml of latex, and 110 μg of RNA was obtained from 1 g of xylem.

(Preparation of cDNA Libraries of Para Rubber Tree)

The cDNA libraries were prepared from the RNA samples derived from *Hevea brasiliensis* latex and xylem by the V-Capping method at Hitachi Instruments Service Co., Ltd. The V-Capping method is a method that can achieve full-length cDNAs at a high percentage.

The cDNA library derived from the latex has the library size of $1.7\times10^5$, the insert percentage of 71% (24 samples/agarose gel electrophoresis), and the percentage of full-length cDNA was 82% (toward clones with insert). The size of cDNA library derived from the xylem was $2.9\times10^5$, and the percentage of insert was 80% (24 samples/agarose gel electrophoresis), and the percentage of full-length cDNA was 87% (toward clones with insert).

(Sequence Analysis, Clustering Analysis and Annotation Analysis of EST Sequences)

At the Genome Information Science Laboratory of Kitasato Institute for Life Sciences of Kitasato University, exhaustive one-pass sequence analysis was performed on approximately 20,000 clones of the cDNA libraries derived from latex and xylem of *Hevea brasiliensis* respectively.

According to the sequence information obtained from the sequence analysis, clones with no insert and clones failed to determine sequence were removed, then high accuracy sequence information was obtained. The latex cDNA library and xylem cDNA library provided 16407 EST sequences and 16305 EST sequences respectively with high accuracy, total 32442.

The obtained partial sequences were subjected to clustering analysis based on similarity between sequences, and annotation analysis based on comparison with known genes, thereby an EST database of *Hevea brasiliensis* was constructed. A VISUALBIO clustering of NTT Software was used for the clustering analysis. The annotation analysis was performed by homology search using NCBI BLAST. The database used for the search was nr (All non-redundant GenBank CDS translations+PDB+SwissProt+PIR (Peptide Sequence Database)).

In the obtained EST database, EST sequences presumed to encode the various enzymes involved in the vitamin E biosynthesis pathway were found, i.e., prephenate dehydratase, another prephenate dehydratase obtained from other clone, p-hydroxyphenyl pyruvic acid dioxygenase, geranylgeranyl reductase, homogentisic acid phytyl transferase, 2-methyl-6-geranylgeranyl benzoquinone methyl transferase, 2-methyl-6-phytyl benzoquinone methyl transferase.

(Sequence Determination at 3'-Terminal by 3'-Race)

The sequences at the 3'-terminal were determined by 3'-RACE (Rapid Amplification of cDNA Ends) on each sequences obtained by the analyses above to obtain full-length cDNAs. For 3'-RACE, a 3'-Full RACE Core Set (Takara Bio Inc.) was used. An oligo-dT primer was used for reverse transcription. For amplification by PCR, an oligo-dT primer and a sense primer having sequence identity with a part of known sequences were used. The amplified fragments were obtained from reverse transcription and PCR, and then the fragments were subjected to TA cloning into pT7Blue vector, which was succeeded by sequence analysis.

(Cloning by Degenerate PCR)

By the alignment of known amino acid sequences of other plants, the degeneration of primer (Degenerate Primer) is designed from the high conservation region, and a partial sequence of the open reading frame (ORF) is acquired by PCR. Furthermore, based on the obtained each partial sequence information, the 3'-terminal sequence by 3'-RACE (Rapid Amplification of cDNA Ends, RACE) and the 5'-terminal sequence by 5'-RACE were determined to obtain full-length cDNAs.

For 3'-RACE, 5'-RACE, respectively, a 3'-Full RACE Core Set, a 5'-Full RACE Core Set (Takara Bio Inc.) were used. An oligo-dT primer was used for reverse transcription. For amplification by the PCR, an oligo-dT primer and a sense primer having sequence identity with a part of known sequences were used. The amplified fragments were obtained from reverse transcription and PCR, and then the fragments were subjected to TA cloning into pT7Blue vector, which was succeeded by sequence analysis. The various enzymes of the intended vitamin E biosynthesis pathway are homogentisic acid geranylgeranyl transferase, tocopherol cyclase, γ-tocopherol methyl transferase which were not found in EST database.

The sequences obtained in this way are as follows; (1) the base sequence of prephenate dehydratase (SEQ ID NO: 1 in the sequence list), (2) the base sequence of prephenate dehydratase obtained from another clone (SEQ ID NO: 3 in the sequence list), (3) the base sequence of p-hydroxyphenyl pyruvic acid dioxygenase (SEQ ID NO: 5 in the sequence list), (4) the base sequence of geranylgeranyl reductase (SEQ ID NO: 7 in the sequence list), (5) the base sequence of homogentisic acid phytyl transferase (SEQ ID NO: 9 in the sequence list), (6) the base sequence of 2-methyl-6-geranylgeranyl benzoquinone methyl transferase (SEQ ID NO: 11 in the sequence list), (7) the base sequence of homogentisic acid geranylgeranyl transferase (SEQ ID NO: 13 in the sequence list), (8) the base sequence of 2-methyl-6-phytyl benzoquinone methyl transferase (SEQ ID NO: 15 in the sequence list), (9) the base sequence of tocopherol cyclase (SEQ ID NO: 17 in the sequence list), and (10) the base sequence of γ-tocopherol methyl transferase (SEQ ID NO: 19 in the sequence list).

Additionally, the deduced amino acid sequences of the proteins obtained from the open reading frames are as follows; (1) the amino acid sequence of prephenate dehydratase (SEQ ID NO:2 in the sequence list), (2) the amino acid sequence of prephenate dehydratase obtained from another clone (SEQ ID NO:4 in the sequence list), (3) the amino acid sequence of p-hydroxyphenyl pyruvic acid dioxygenase (SEQ ID NO:6 in the sequence list), (4) the amino acid sequence of geranylgeranyl reductase (SEQ ID NO:8 in the sequence list), (5) the amino acid sequence of homogentisic acid phytyl transferase (SEQ ID NO:10 in the sequence list), (6) the amino acid sequence of 2-methyl-6-geranylgeranyl benzoquinone methyl transferase (SEQ ID NO:12 in the sequence list), (7) the amino acid sequence of homogentisic acid geranylgeranyl transferase (SEQ ID NO:14 in the sequence list), (8) the amino acid sequence of 2-methyl-6-phytyl benzoquinone methyl transferase (SEQ ID NO:16 in the sequence list), (9) the amino acid sequence of tocopherol cyclase (SEQ ID NO:18 in the sequence list), and (10) the amino acid sequence of γ-tocopherol methyl transferase (SEQ ID NO: 20 in the sequence list).

(Vitamin E Analysis)

For total 8 substances of 4 kinds of tocotrienol and 4 kinds of tocopherol included in the young leave, mature leave, fresh latex of Para rubber tree, the contents were quantified in HPLC.

From fresh latex, a solid rubber was obtained by drying under reduced pressure. The solid rubber was chipped and weighed, and then Soxhlet extraction was performed by acetone. The solvent was distilled away, and the extracted material was dissolved in hexane to obtain a sample for analysis. After weighting leaves, 1% (w/v) sodium chloride solution, 3% pyrogallol-ethanol solution, 60% (w/v) potassium hydroxide were added and the leaves were saponified at 70° C. for 30 minutes. The solvent of hexane: 2-propanol: ethyl acetate (18:3:2) was added and the resultant material was centrifuged. The solvent was distilled away, and the resultant material was dissolved in hexane to obtain a sample for analysis.

The analysis conditions of HPLC are as follows.

| | |
|---|---|
| Column | YMC-Pack SIL-06 |
| Column temperature | 40° C. |
| Flow rate | 1.5 ml/min |
| Moving bed | Hexane + 2-propanol + acetic acid (1000:6:5) |
| Detector | Fluorimetry<br>(Excitation wavelength 298 nm, measurement wavelength 325 nm) |

Figure 22:
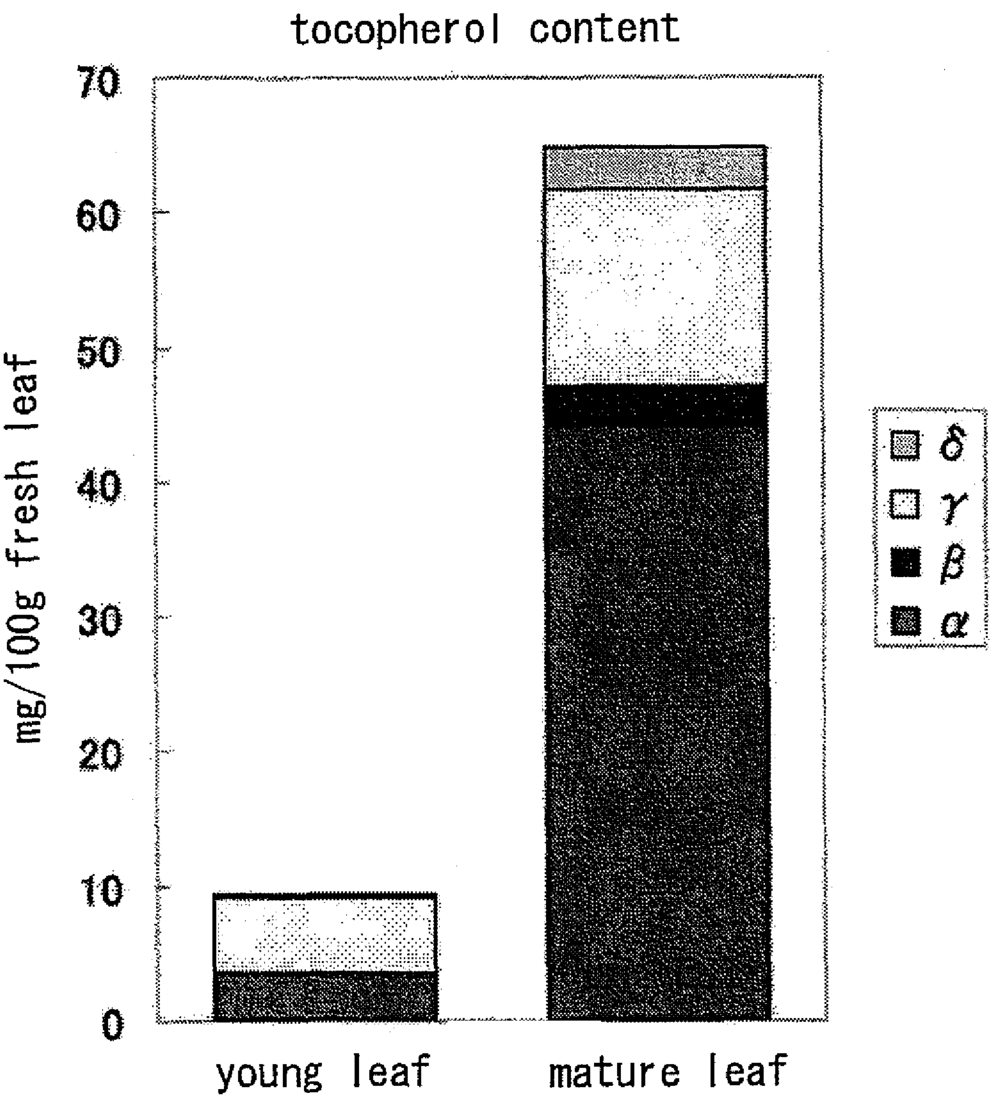
FIG. 22 shows a graph of the tocopherol content included in the leaf of Para rubber tree.
Figure 23:
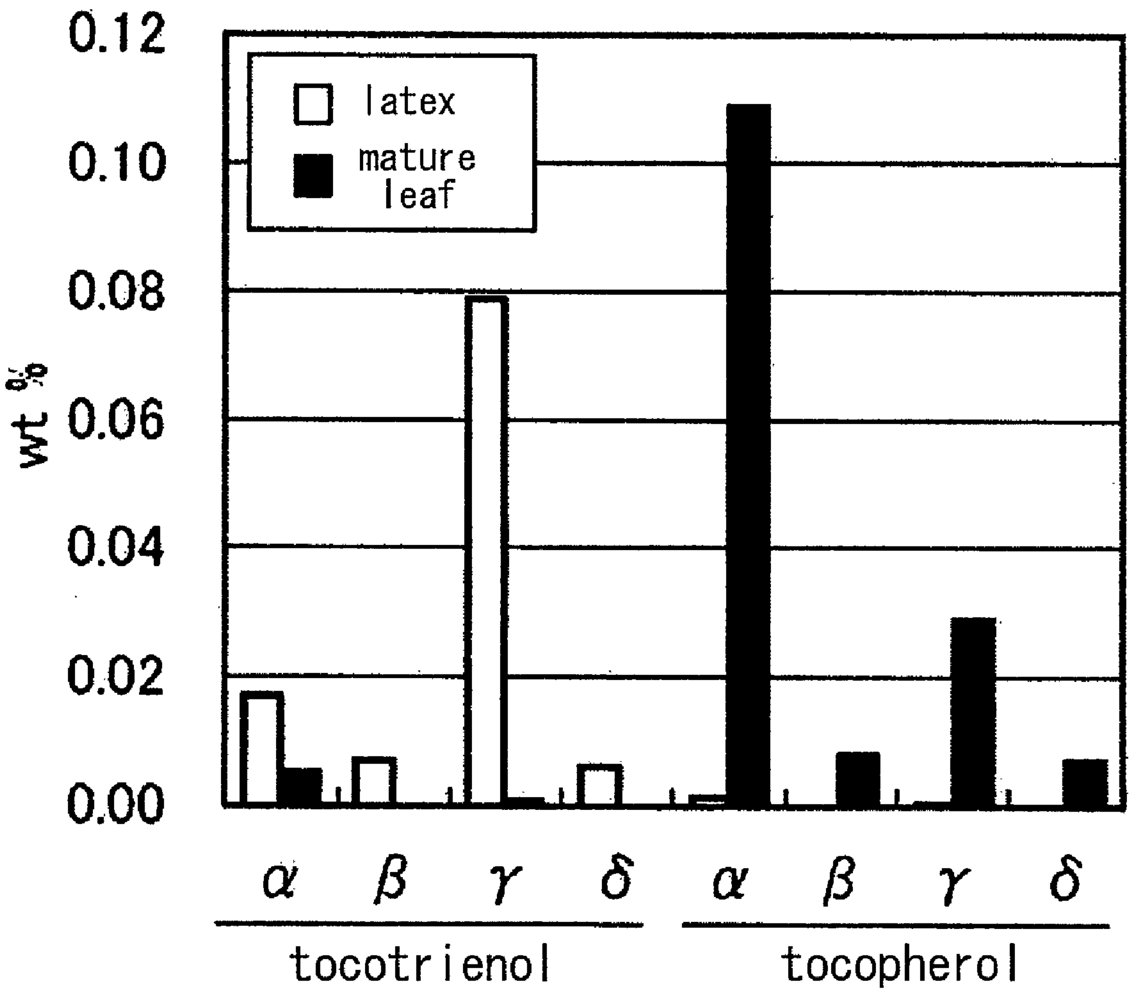
FIG. 23 shows a graph of contents of tocopherol and tocotrienol included in a mature leaf and latex of Para rubber tree.

FIGS. 22 and 23 show the result of analysis in HPLC. FIG. 22 is a graph showing the tocopherol content included in leaves, and FIG. 23 is a graph showing a content of the tocopherol and tocotrienol included in mature leaves and latex of Para rubber tree. As shown in FIGS. 22 and 23, the leaves contained much tocopherol, and on the other hand, the dry rubber contained much tocotrienol. In addition, with the maturity of the leaf, the amount of tocopherol in leaf was increased (FIG. 22). The composition of tocopherol in leaf included the most α, and in the order corresponding to γ, δ, β (FIG. 22). On the other hand, the composition of tocotrienol in latex included the most γ, and the in the order corresponding to α, β, δ (FIG. 23).

(Expression Level Analysis of Each Gene)

Figure 24:
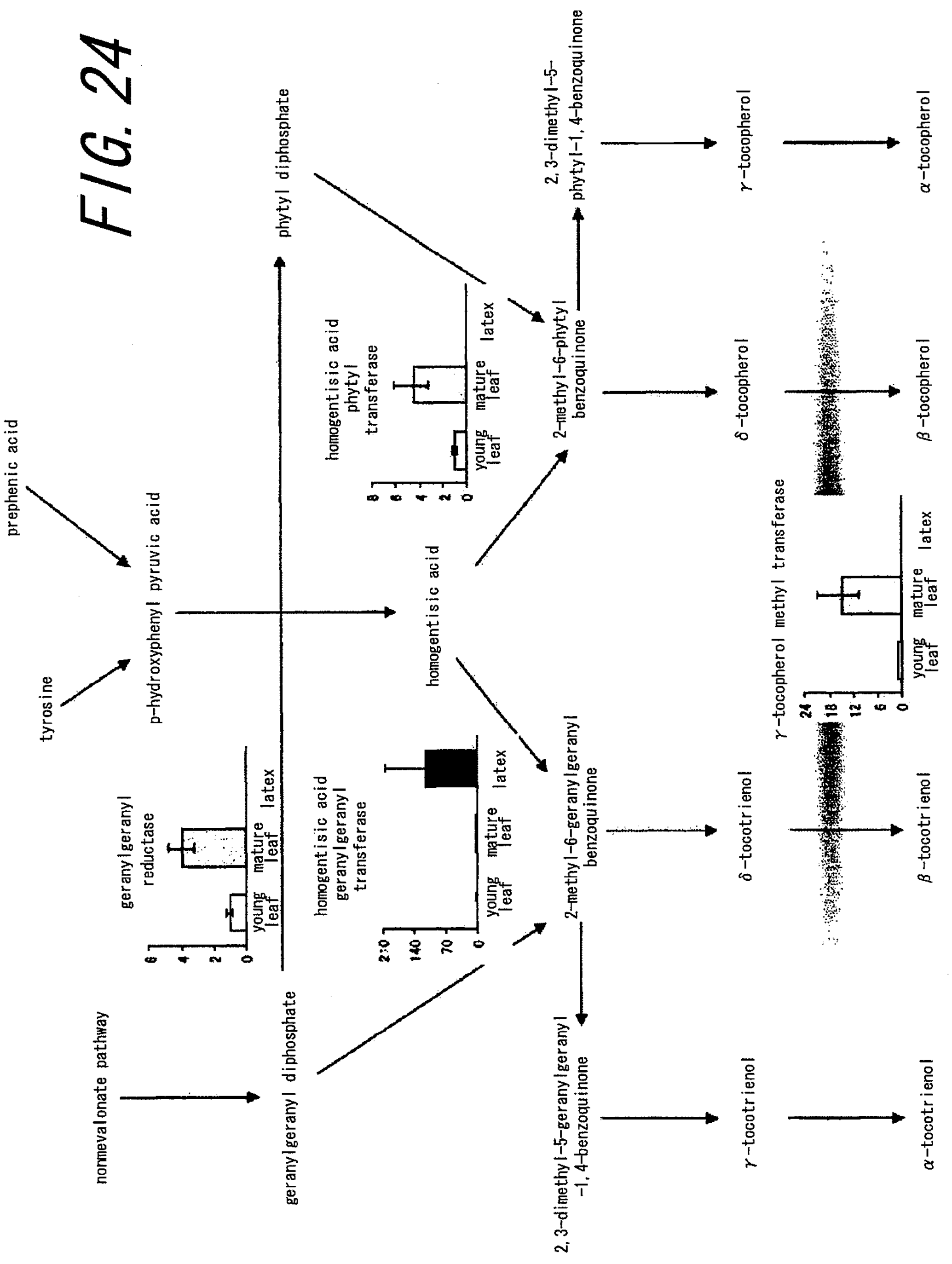
FIG. 24 shows a result of expression level analysis of each gene of this invention in each tissue of Para rubber tree.

Using a primer specific for a template of the cDNA which prepared from each tissue of Para rubber tree, the expression level of each gene was analyzed by Realtime PCR in GeneAmp 5700 Sequence Detection System (Applied Biosystems). The result is shown in FIG. 24. Referring to FIG. 24, it was revealed that the geranylgeranyl reductase and homogentisic acid phytyl transferase, which play an important role in the biosynthesis of tocopherol, were expressed much in leaf and the homogentisic acid geranylgeranyl transferase, which plays an important role in the biosynthesis of tocotrienol, was expressed in latex. In other words, it was suggested that there is a possibility that the content of tocotrienol and tocopherol could be regulated by controlling these gene expressions. In addition, it was revealed that the γ-tocopherol methyl transferase was expressed more in leaf. In other words, it was suggested that there is a possibility that the composition of α and γ, δ and β could be regulated by controlling this gene expression.

(Example of Validated Function Using Model Plants)

*Periploca* (*Periploca sepium* Bunge), which is the model plant of the rubber-producing plant, can growth earlier than Para rubber tree (it grow up to a mature tree in a half year to one year), and therefore in *Periploca*, the gene introduction can be confirm earlier than Para rubber tree. Furthermore, *Periploca* is similar to Para rubber tree in the structure and function of latex tube and it is considered that in *Periploca*, the enzymes of vitamin E biosynthesis pathway similar to Para rubber tree are functioned. Therefore, the gene concerned functions in the Para rubber tree is expected to function when the genes involved in vitamin E biosynthesis of this invention function in *Periploca*. In addition, it is confirmed by analysis that *Periploca* originally includes only tocopherol, and it is expected that composition and content of the vitamin E may be changed by genetic recombination. Therefore, in this embodiment, *Periploca* was used as an object for transfer of genes according to this invention.

Figure 25:
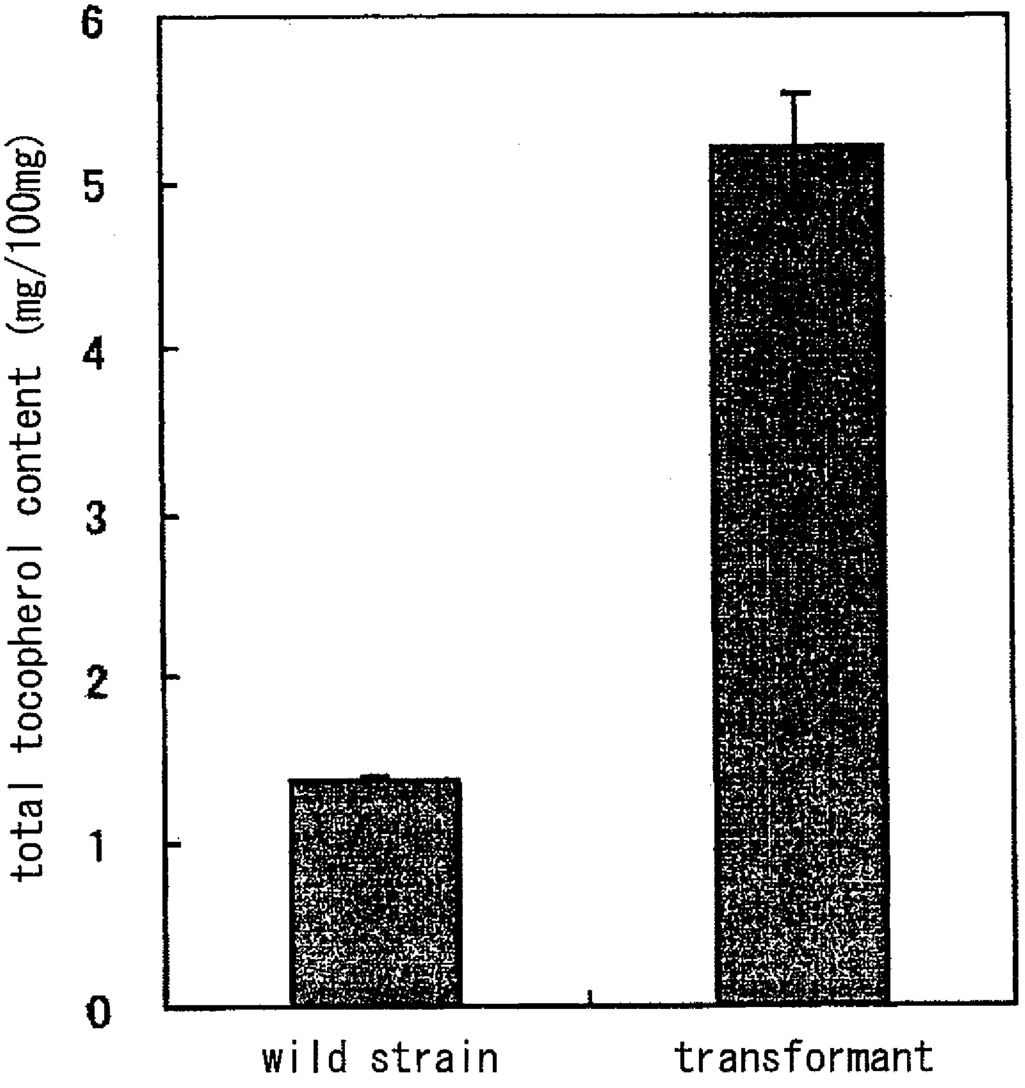
FIG. 25 shows a result of extracted vitamin E from Periploca transformant into which a gene of this invention was introduced.

Among the full-length vitamin E biosynthesis related genes of Para rubber tree provided in the procedure mentioned above, as to the p-hydroxyphenyl pyruvic acid dioxygenase, the gene was transfected into *Periploca* to manufacture a genetically modified plant and their functions were confirmed by measuring the composition, content of those vitamin E. By the PCR using sense primer and antisense primer with addition of a suitable restriction enzyme site, the sequence of coding region of the purpose gene of the Para rubber tree was amplified. The amplified fragment was cloned in pMSIsGFP vector retaining a sGFP gene and kanamycin-resistant gene. This vector was introduced into *Agrobacterium* and a planta of *Periploca* was infected. The selection of transformant was carried out by observation of fluorescence imaging of sGFP as a marker. Furthermore, Genomic DNA was extracted from the transformant and it was confirmed by PCR whether or not there was an introduction of the purpose gene. The result was shown in FIG. 25. Referring to FIG. 25, the vitamin E was extracted from the resultant *Periploca* transformant so that the significant increase of content was recognized. As a result, the function analysis using *Periploca* transformant was able to specify gene function.

INDUSTRIAL APPLICABILITY

According to the invention, genes encoding a series of enzymes involved in the vitamin E biosynthesis in Para rubber tree (*Hevea brasiliensis*) were taken and the base sequences of these genes were determined. Since vitamin E is an antioxidant existing in nature, it is expected that transformation of a plant by using the genes obtained in the invention would result in an increase in the vitamin E content of the plant, and consequently the rubber can be prevented from aging.

The invention claimed is:

1. An isolated protein selected from the group consisting of:

(a) an isolated protein comprising the amino acid sequence of SEQ ID NO: 14, and (b) an isolated protein comprising an amino acid sequence having at least 95% amino acid sequence identity with the amino acid sequence of SEQ ID NO: 14, wherein the isolated protein has homogentisic acid geranylgeranyl transferase activity.

* * * * *